United States Patent [19]
Trowern et al.

[11] Patent Number: 6,162,903
[45] Date of Patent: Dec. 19, 2000

[54] IMMUNOGLOBULIN BINDING PROTEINS DERIVED FROM L PROTEIN AND THEIR USES

[75] Inventors: Angus R. Trowern, Southampton; Antony Atkinson, Salisbury; Jonathan P. Murphy, Henley-on-Thames; Oliver S. Laurence, Winchester; Clive J. Duggleby, Middle Winterslow, all of United Kingdom

[73] Assignee: Actinova Limited, Cambridge, United Kingdom

[21] Appl. No.: 08/446,137

[22] Filed: May 22, 1995

Related U.S. Application Data

[63] Continuation of application No. 08/331,640, filed as application No. PCT/GB93/00950, May 7, 1993, abandoned.

[30] Foreign Application Priority Data

May 7, 1992 [GB] United Kingdom .................... 9209804
Dec. 24, 1992 [GB] United Kingdom .................... 9226928

[51] Int. Cl.[7] .................................................. C07K 16/00
[52] U.S. Cl. .............................. 530/388.25; 530/388.25; 435/68
[58] Field of Search .......................... 435/68; 530/388.25

[56] References Cited

U.S. PATENT DOCUMENTS 4,876,194 10/1989 Bjorck et al. ............................. 435/68
5,502,022 3/1996 Schwarz et al. ........................ 502/401

FOREIGN PATENT DOCUMENTS 0 255 497 A2 2/1988 European Pat. Off. .
9322439 11/1993 WIPO .

OTHER PUBLICATIONS

B.H.K. Nilson et al. "Protein L from Peptostreptococcus magnue binds . . . " The Journal of Biological Chemistry, vol. 267, No. 4, issue on Feb. 5, 1992, pp. 2234–2239.

W. Kastern et al. "Protein L, a bacterial immunoglobulin–binding . . . " Infection and Immunity, vol. 58 No. 5, May 1990, pp. 1217–1222.

B. Äkerström et al. "Protein L: an immunoglobulin light chain–binding . . . " The Journal of Biological Chemistry, vol. 264 No. 33, Issue of Nov. 25, 1989, pp. 19740–19746.

Lewin, Roger, Science, vol. 237, p. 1570, 1987.

Reeck, Gerald R. et al, Cell, vol. 50, Aug. 28, 1987, p. 667.

Lewin, R, Science, vol. 237, p. 1570, 1987.

Reeck, G R et al, Cell, Aug. 28, vol. 50, p. 667, 1987.

Akerstrom, B et al, J. of Biological Chemistry vol. 264, No. 33, Nov. 25, p. 19740–19746, 1989.

Bjorck, Lars, J. of Immun., vol. 140, No. 4, p. 1194–1197, Feb. 15, 1988.

Chateau, MDe, et al, Scad. J. Immunol., vol. 37, p. 399–405, 1993.

Elbashir, M.I et al, J. Immunol. Methods, vol. 135, p. 171–179, 1990.

Kastern, W et al, J. of Biolog. Chem. vol. 267(18) Jun. 25, p. 12820–12825, 1992.

Kastern, W et al, Infect. Immun., May, vol. 58(5), p. 1217–1222, 1990.

Kihlberg, B. et al, J. Biolog. Chem., vol. 267(35) Dec. 15, p. 25583–25588, 1992.

Lammler, C et al, Can. J. Microbiolog., vol. 35, p. 614–618, 1989.

Ng, L et al, J. Gen. Microbiol, vol. 137, pp. 1323–1331, 1991.

Nilson, Bo H. K et al, J. Biolog. Chem., vol. 267 No. 4, p. 2234–2239, Feb. 5, 1992.

Patella, V et al, J. Immun., Nov. 1, vol. 145(9), p. 3054–3061, 1990.

*Primary Examiner*—Lynette R. F. Smith
*Assistant Examiner*—Ginny Allen Portner
*Attorney, Agent, or Firm*—Seed IP Law Group

[57] ABSTRACT

Synthetic molecules are provided comprising one or more immunoglobulin binding domains as well as sequences which have at least 90% homology to these domains.

9 Claims, 10 Drawing Sheets

```
TTTGGACAGT GGACGAAACA AGAACACTGA TTTAATAAAT TGGTGAAATT CGATTGTTGA    60

AATACCTTTT TGGGTAGAAA TAACTAAGGA ATGGCAATAT AA TTG CTT GGA AAC     114
                                              Leu Leu Gly Asn
                                              -59

GAA TTT GAT TTA AAT AGC ATT AAA TGC AAA AAA TTT AAA AGG AGG AGA    162
Glu Phe Asp Leu Asn Ser Ile Lys Cys Lys Lys Phe Lys Arg Arg Arg
-55             -50              -45              -40
                                                          ┌─SS
CAA ATT CCA CCC TTT ATA AAG GGA AGT TTC CAT TGT CAA AAT AAT│ATG    210
Gln Ile Pro Pro Phe Ile Lys Gly Ser Phe His Cys Gln Asn Asn Met
            -35              -30              -25

AAG ATT AAT AAG AAA TTA TTA ATG GCT GCA CTT GCA GGA GCA ATT GTA    258
Lys Ile Asn Lys Lys Leu Leu Met Ala Ala Leu Ala Gly Ala Ile Val
            -20              -15              -10
                          ┌─M
GTT GGT GGT GGA GCT AAC GCT│TAC GCA GCT GAA GAA GAT AAC ACT GAT    306
Val Gly Gly Gly Ala Asn Ala Tyr Ala Ala Glu Glu Asp Asn Thr Asp
            -5               1               5

AAT AAC CTT TCA ATG GAT GAA ATT AGT GAT GCT TAT TTT GAT TAT CAC    354
Asn Asn Leu Ser Met Asp Glu Ile Ser Asp Ala Tyr Phe Asp Tyr His
 10              15              20              25

GGA GAT GTT TCA GAT TCA GTA GAT CCT GTA GAA GAA GAA ATA GAC GAA    402
Gly Asp Val Ser Asp Ser Val Asp Pro Val Glu Glu Glu Ile Asp Glu
             30              35              40

GCA TTA GCA AAA GCA TTA GCA GAA GCT AAA GAA ACA GCA AAA AAA CAT    450
Ala Leu Ala Lys Ala Leu Ala Glu Ala Lys Glu Thr Ala Lys Lys His
             45              50              55
                                            ┌─A1
ATA GAT TCT TTA AAT CAT TTG TCA GAA ACA GCA AAA AAA│TTA GCT AAG    498
Ile Asp Ser Leu Asn His Leu Ser Glu Thr Ala Lys Lys Leu Ala Lys
             60              65              70

AAT GAT ATA GAT TCA GCT ACT ACT ATT AAT GCA ATC AAT GAC ATC GTA    546
Asn Asp Ile Asp Ser Ala Thr Thr Ile Asn Ala Ile Asn Asp Ile Val
             75              80              85
```

*Fig. 1*

```
                                    ┌─B1
GCA AGA GCA GAT GTA ATG GAA AGA AAA│ACA GCT GAA AAA GAA GAA GCA        594
Ala Arg Ala Asp Val Met Glu Arg Lys Thr Ala Glu Lys Glu Glu Ala
 90               95               100              105

GAA AAA TTA GCA GCA GCA AAA GAA ACA GCA AAG AAA CAT ATA GAT GAA        642
Glu Lys Leu Ala Ala Ala Lys Glu Thr Ala Lys Lys His Ile Asp Glu
                 110              115              120
                                        ┌─A2
TTA AAA CAC TTA GCA GAC AAA ACA AAA GAA│TTA GCT AAG AGA GAT ATA        690
Leu Lys His Leu Ala Asp Lys Thr Lys Glu Leu Ala Lys Arg Asp Ile
             125              130              135

GAT TCA GCT ACT ACT ATT AAT GCA ATC AAT GAC ATC GTA GCA AGA GCA        738
Asp Ser Ala Thr Thr Ile Asn Ala Ile Asn Asp Ile Val Ala Arg Ala
             140              145              150
                            ┌─B2
GAT GTA ATG GAA AGA AAA│ACA GCT GAA AAA GAA GAA GCA GAA AAA TTA        786
Asp Val Met Glu Arg Lys Thr Ala Glu Lys Glu Glu Ala Glu Lys Leu
             155              160              165

GCA GCA GCA AAA GAA ACA GCA AAG AAA CAT ATA GAT GAA TTA AAA CAC        834
Ala Ala Ala Lys Glu Thr Ala Lys Lys His Ile Asp Glu Leu Lys His
170              175              180              185
                                    ┌─A3
TTA GCA GAC AAA ACA AAA GAA│TTA GCT AAG AGA GAT ATA GAT TCA GCT        882
Leu Ala Asp Lys Thr Lys Glu Leu Ala Lys Arg Asp Ile Asp Ser Ala
                 190              195              200

ACT ACT ATT GAT GCA ATC AAT GAT ATC GTA GCT AGA GCA GAT GTA ATG        930
Thr Thr Ile Asp Ala Ile Asn Asp Ile Val Ala Arg Ala Asp Val Met
             205              210              215
                    ┌─C1
GAA AGA AAG TTA TCT GAA│AAA GAA ACA CCA GAA CCA GAA GAA GAA GTT        978
Glu Arg Lys Leu Ser Glu Lys Glu Thr Pro Glu Pro Glu Glu Glu Val
             220              225              230

ACA ATC AAA GCT AAC TTA ATC TTT GCA GAT GGA AGC ACA CAA AAT GCA       1026
Thr Ile Lys Ala Asn Leu Ile Phe Ala Asp Gly Ser Thr Gln Asn Ala
         235              240              245
                        ┌─Z1
GAA TTC AAA GGA ACA TTC│GCA AAA GCA GTA TCA GAT GCT TAC GCT TAC       1074
Glu Phe Lys Gly Thr Phe Ala Lys Ala Val Ser Asp Ala Tyr Ala Tyr
250              255              260              265
```

*Fig. 1 CONTINUED*

```
GCA GAT GCT TTA AAG AAA GAC AAC GGA GAA TAT ACT GTA GAC GTT GCA     1122
Ala Asp Ala Leu Lys Lys Asp Asn Gly Glu Tyr Thr Val Asp Val Ala
            270             275             280
                                                ┌─C2
GAT AAA GGC TTA ACT TTA AAT ATT AAA TTC GCT GGT AAA│AAA GAA AAA     1170
Asp Lys Gly Leu Thr Leu Asn Ile Lys Phe Ala Gly Lys Lys Glu Lys
            285             290             295

CCA GAA GAA CCA AAA GAA GAA GTT ACA ATC AAA GTT AAC TTA ATC TTT     1218
Pro Glu Glu Pro Lys Glu Glu Val Thr Ile Lys Val Asn Leu Ile Phe
            300             305             310
                                                    ┌─Z2
GCA GAT GGA AAG ACA CAA ACA GCA GAA TTC AAA GGA ACA TTT│GAA GAA     1266
Ala Asp Gly Lys Thr Gln Thr Ala Glu Phe Lys Gly Thr Phe Glu Glu
            315             320             325

GCA ACA GCA AAA GCT TAT GCT TAT GCA GAC TTA TTA GCA AAA GAA AAT     1314
Ala Thr Ala Lys Ala Tyr Ala Tyr Ala Asp Leu Leu Ala Lys Glu Asn
330             335             340             345

GGC GAA TAT ACA GCA GAC TTA GAA GAT GGT GGA AAC ACA ATC AAC ATT     1362
Gly Glu Tyr Thr Ala Asp Leu Glu Asp Gly Gly Asn Thr Ile Asn Ile
            350             355             360
                ┌─C3
AAA TTT GCT GGA│AAA GAA ACA CCA GAA ACA CCA GAA GAA CCA AAA GAA     1410
Lys Phe Ala Gly Lys Glu Thr Pro Glu Thr Pro Glu Glu Pro Lys Glu
            365             370             375

GAA GTT ACA ATC AAA GTT AAC TTA ATC TTT GCA GAT GGA AAG ATA CAA     1458
Glu Val Thr Ile Lys Val Asn Leu Ile Phe Ala Asp Gly Lys Ile Gln
            380             385             390
                            ┌─Z3
ACA GCA GAA TTC AAA GGA ACA TTT│GAA GAA GCA ACA GCA AAA GCT TAT     1506
Thr Ala Glu Phe Lys Gly Thr Phe Glu Glu Ala Thr Ala Lys Ala Tyr
            395             400             405

GCT TAT GCA AAC TTA TTA GCA AAA GAA AAT GGC GAA TAT ACA GCA GAC     1554
Ala Tyr Ala Asn Leu Leu Ala Lys Glu Asn Gly Glu Tyr Thr Ala Asp
410             415             420             425
                                                    ┌─C4
TTA GAA GAT GGT GGA AAC ACA ATC AAC ATT AAA TTT GCT GGA│AAA GAA     1602
Leu Glu Asp Gly Gly Asn Thr Ile Asn Ile Lys Phe Ala Gly Lys Glu
            430             435             440
```

*Fig. 1 CONTINUED*

```
ACA CCA GAA ACA CCA GAA GAA CCA AAA GAA GAA GTT ACA ATC AAA GTT         1650
Thr Pro Glu Thr Pro Glu Glu Pro Lys Glu Glu Val Thr Ile Lys Val
            445             450             455

AAC TTA ATC TTT GCA GAT GGA AAA ACA CAA ACA GCA GAA TTC AAA GGA         1698
Asn Leu Ile Phe Ala Asp Gly Lys Thr Gln Thr Ala Glu Phe Lys Gly
            460             465             470
        ┌─Z4
ACA TTT │GAA GAA GCA ACA GCA GAA GCT TAC AGA TAT GCA GAC TTA TTA         1746
Thr Phe Glu Glu Ala Thr Ala Glu Ala Tyr Arg Tyr Ala Asp Leu Leu
        475             480             485

GCA AAA GTA AAT GGT GAA TAC ACA GCA GAC TTA GAA GAT GGC GGA TAC         1794
Ala Lys Val Asn Gly Glu Tyr Thr Ala Asp Leu Glu Asp Gly Gly Tyr
    490             495             500             505
                                    ┌─D1
ACT ATC AAC ATC AAA TTT GCT GGA AAA │GAA CAA CCA GGC GAA AAT CCA         1842
Thr Ile Asn Ile Lys Phe Ala Gly Lys Glu Gln Pro Gly Glu Asn Pro
                510             515             520

GGA ATC ACA ATT GAT GAA TGG TTA TTA AAG AAT GCT AAA GAA GAA GCA         1890
Gly Ile Thr Ile Asp Glu Trp Leu Leu Lys Asn Ala Lys Glu Glu Ala
            525             530             535

ATC AAA GAA TTA AAA GAA GCA GGA ATC ACT TCT GAT TTA TAC TTC AGC         1938
Ile Lys Glu Leu Lys Glu Ala Gly Ile Thr Ser Asp Leu Tyr Phe Ser
            540             545             550

TTA ATC AAT AAA GCA AAA ACA GTT GAA GGC GTA GAA GCA TTA AAG AAC         1986
Leu Ile Asn Lys Ala Lys Thr Val Glu Gly Val Glu Ala Leu Lys Asn
        555             560             565

GAA ATC TTA AAA GCA CAC GCT GGA GAA GAA ACA CCA GAA TTA AAA GAT         2034
Glu Ile Leu Lys Ala His Ala Gly Glu Glu Thr Pro Glu Leu Lys Asp
570             575             580             585

GGA TAT GCA ACA TAT GAA GAA GCA GAA GCA GCA GCT AAA GAA GCT TTG         2082
Gly Tyr Ala Thr Tyr Glu Glu Ala Glu Ala Ala Ala Lys Glu Ala Leu
                590             595             600

AAA AAT GAT GAT GTT AAC AAC GCA TAC GAA ATA GTT CAA GGT GCA GAC         2130
Lys Asn Asp Asp Val Asn Asn Ala Tyr Glu Ile Val Gln Gly Ala Asp
            605             610             615
```

*Fig. 1 CONTINUED*

```
GGA AGA TAC TAC TAT GTA TTA AAG ATT GAA GTT GCA GAC GAA GAA GAA        2178
Gly Arg Tyr Tyr Tyr Val Leu Lys Ile Glu Val Ala Asp Glu Glu Glu
         620                 625                 630
                                              ┌─E2
CCA GGT GAA GAC ACT CCA GAA GTT CAA GAA┌GGT TAC GCA ACT TAC GAA        2226
Pro Gly Glu Asp Thr Pro Glu Val Gln Glu Gly Tyr Ala Thr Tyr Glu
     635                 640                 645

GAA GCA GAA GCA GCA GCT AAA GAA GCA TTA AAA GAA GAT AAA GTT AAC        2274
Glu Ala Glu Ala Ala Ala Lys Glu Ala Leu Lys Glu Asp Lys Val Asn
650                 655                 660                 665

AAT GCA TAC GAA GTA GTT CAA GGT GCA GAC GGA AGA TAC TAC TAT GTA        2322
Asn Ala Tyr Glu Val Val Gln Gly Ala Asp Gly Arg Tyr Tyr Tyr Val
                 670                 675                 680
                                     ┌─D2
TTA AAA ATC GAA GAT AAA GAA GAT┌GAA CAA CCA GGT GAA GAA CCA GGC        2370
Leu Lys Ile Glu Asp Lys Glu Asp Glu Gln Pro Gly Glu Glu Pro Gly
             685                 690                 695

GAA AAC CCA GGA ATC ACA ATT GAT GAA TGG TTA TTA AAG AAT GCT AAA        2418
Glu Asn Pro Gly Ile Thr Ile Asp Glu Trp Leu Leu Lys Asn Ala Lys
         700                 705                 710

GAA GAC GCA ATC AAA GAA TTA AAA GAA GCA GGA ATC AGT TCT GAC ATA        2466
Glu Asp Ala Ile Lys Glu Leu Lys Glu Ala Gly Ile Ser Ser Asp Ile
     715                 720                 725

TAC TTT GAT GCA ATC AAC AAA GCA AAA ACA GTA GAA GGC GTA GAA GCG        2514
Tyr Phe Asp Ala Ile Asn Lys Ala Lys Thr Val Glu Gly Val Glu Ala
730                 735                 740                 745
                                          ┌─D3
TTA AAG AAC GAA ATC TTA AAA GCA CAC GCT┌GAA AAA CCA GGC GAA AAC        2562
Leu Lys Asn Glu Ile Leu Lys Ala His Ala Glu Lys Pro Gly Glu Asn
                 750                 755                 760

CCA GGA ATC ACA ATT GAT GAA TGG TTA TTA AAG AAT GCT AAA GAA GCT        2610
Pro Gly Ile Thr Ile Asp Glu Trp Leu Leu Lys Asn Ala Lys Glu Ala
             765                 770                 775

GCA ATC AAA GAA TTA AAA GAA GCA GGA ATC ACT GCT GAA TAT CTA TTC        2658
Ala Ile Lys Glu Leu Lys Glu Ala Gly Ile Thr Ala Glu Tyr Leu Phe
         780                 785                 790
```

*Fig. 1 CONTINUED*

```
AAC TTA ATC AAC AAA GCA AAA ACA GTA GAA GGC GTA GAA TCA TTA AAG        2706
Asn Leu Ile Asn Lys Ala Lys Thr Val Glu Gly Val Glu Ser Leu Lys
        795             800             805
                                    ┌─D4
AAC GAA ATC TTA AAA GCA CAC GCT│GAA AAA CCA GGC GAA AAC CCA GGA        2754
Asn Glu Ile Leu Lys Ala His Ala Glu Lys Pro Gly Glu Asn Pro Gly
810             815             820             825

ATC ACA ATT GAT GAA TGG TTA TTA AAG AAC GCT AAA GAA GAT GCA ATT        2802
Ile Thr Ile Asp Glu Trp Leu Leu Lys Asn Ala Lys Glu Asp Ala Ile
            830             835             840

AAA GAA TTA AAA GAA GCA GGA ATT ACT TCT GAC ATA TAC TTT GAT GCT        2850
Lys Glu Leu Lys Glu Ala Gly Ile Thr Ser Asp Ile Tyr Phe Asp Ala
            845             850             855

ATC AAC AAA GCA AAA ACT ATT GAA GGC GTA GAA GCA TTA AAG AAT GAA        2898
Ile Asn Lys Ala Lys Thr Ile Glu Gly Val Glu Ala Leu Lys Asn Glu
        860             865             870
                            ┌─R1                     ┌─R2
ATC TTA AAG GCT CAT│AAA AAA GAT GAA GAA CCA GGT│AAA AAA CCA GGT        2946
Ile Leu Lys Ala His Lys Lys Asp Glu Glu Pro Gly Lys Lys Pro Gly
    875             880             885
    ┌─R3                 ┌─R4                 ┌─R5
GAA GAC│AAA AAA CCA GAA GAT│AAA AAA CCA GGT GAA GAT│AAA AAA CCA        2994
Glu Asp Lys Lys Pro Glu Asp Lys Lys Pro Gly Glu Asp Lys Lys Pro
890             895             900                     905
        ┌─R6                 ┌─R7                 ┌─R8
GAA GAC│AAA AAA CCT GGT GAA GAT│AAA AAA CCA GAA GAC│AAA AAA CCA        3042
Glu Asp Lys Lys Pro Gly Glu Asp Lys Lys Pro Glu Asp Lys Lys Pro
                910             915             920

GGT AAA ACA GAT AAA GAT TCT CCA AAT AAG AAG AAA AAA GCT AAA TTA        3090
Gly Lys Thr Asp Lys Asp Ser Pro Asn Lys Lys Lys Lys Ala Lys Leu
            925             930             935
```

*Fig. 1 CONTINUED*

```
CCA AAA GCT GGT AGC GAA GCT GAA ATC TTA ACA TTA GCA GCA GCA GCT    3138
Pro Lys Ala Gly Ser Glu Ala Glu Ile Leu Thr Leu Ala Ala Ala Ala
        940                 945                 950

TTA TCA ACA GCA GCA GGT GCT TAC GTT TCA CTT AAA AAA CCT AAA TAA    3186
Leu Ser Thr Ala Ala Gly Ala Tyr Val Ser Leu Lys Lys Pro Lys
        955                 960                 965

TTAATCTTAG ATAAAGAATA GATTAATATA AAAAATGGGA CTTATAATAG TCCCATTTTT   3246

TAATGCGAAA AACTGATACA AAAAATGTAT CAG                               3279
```

*Fig. 1 CONTINUED*

```
       ┌─C1
       ┌ATG GAA ACA CCA GAA CCA GAA GAA GAA GTT ACA ATC AAA GCT AAC TTA      48
        Met Glu Thr Pro Glu Pro Glu Glu Glu Val Thr Ile Lys Ala Asn Leu
        1               5                   10                  15

ATC TTT GCA GAT GGA AGC ACA CAA AAT GCA GAA TTC AAA GGA ACA TTC      96
        Ile Phe Ala Asp Gly Ser Thr Gln Asn Ala Glu Phe Lys Gly Thr Phe
                        20                  25                  30
       ┌─Z1
       ┌GCA AAA GCA GTA TCA GAT GCT TAC GCT TAC GCA GAT GCT TTA AAG AAA     144
        Ala Lys Ala Val Ser Asp Ala Tyr Ala Tyr Ala Asp Ala Leu Lys Lys
                        35                  40                  45

GAC AAC GGA GAA TAT ACT GTA GAC GTT GCA GAT AAA GGC TTA ACT TTA     192
        Asp Asn Gly Glu Tyr Thr Val Asp Val Ala Asp Lys Gly Leu Thr Leu
                50                  55                  60

┌─C2
        AAT ATT AAA TTC GCT GGT AAA┌AAA GAA AAA CCA GAA GAA CCA AAA GAA     240
        Asn Ile Lys Phe Ala Gly Lys Lys Glu Lys Pro Glu Glu Pro Lys Glu
        65                  70                  75                  80

GAA GTT ACA ATC AAA GTT AAC TTA ATC TTT GCA GAT GGA AAG ACA CAA     288
        Glu Val Thr Ile Lys Val Asn Leu Ile Phe Ala Asp Gly Lys Thr Gln
                        85                  90                  95
                                    ┌─Z2
        ACA GCA GAA TTC AAA GGA ACA TTT┌GAA GAA GCA ACA GCA AAA GCT TAT     336
        Thr Ala Glu Phe Lys Gly Thr Phe Glu Glu Ala Thr Ala Lys Ala Tyr
                        100                 105                 110

GCT TAT GCA GAC TTA TTA GCA AAA GAA AAT GGC GAA TAT ACA GCA GAC     384
        Ala Tyr Ala Asp Leu Leu Ala Lys Glu Asn Gly Glu Tyr Thr Ala Asp
                        115                 120                 125
                                                            ┌─C3
        TTA GAA GAT GGT GGA AAC ACA ATC AAC ATT AAA TTT GCT GGA┌AAA GAA     432
        Leu Glu Asp Gly Gly Asn Thr Ile Asn Ile Lys Phe Ala Gly Lys Glu
                130                 135                 140

ACA CCA GAA ACA CCA GAA GAA CCA AAA GAA GAA GTT ACA ATC AAA GTT     480
        Thr Pro Glu Thr Pro Glu Glu Pro Lys Glu Glu Val Thr Ile Lys Val
        145                 150                 155                 160

AAC TTA ATC TTT GCA GAT GGA AAG ATA CAA ACA GCA GAA TTC AAA GGA     528
        Asn Leu Ile Phe Ala Asp Gly Lys Ile Gln Thr Ala Glu Phe Lys Gly
                        165                 170                 175
```

*Fig. 2*

```
                    ┌─Z3
ACA TTT┌GAA GAA GCA ACA GCA AAA GCT TAT GCT TAT GCA AAC TTA TTA         576
Thr Phe Glu Glu Ala Thr Ala Lys Ala Tyr Ala Tyr Ala Asn Leu Leu
            180                 185                 190

GCA AAA GAA AAT GGC GAA TAT ACA GCA GAC TTA GAA GAT GGT GGA AAC         624
Ala Lys Glu Asn Gly Glu Tyr Thr Ala Asp Leu Glu Asp Gly Gly Asn
            195                 200                 205
                                    ┌─C4
ACA ATC AAC ATT AAA TTT GCT GGA┌AAA GAA ACA CCA GAA ACA CCA GAA         672
Thr Ile Asn Ile Lys Phe Ala Gly Lys Glu Thr Pro Glu Thr Pro Glu
            210                 215                 220

GAA CCA AAA GAA GAA GTT ACA ATC AAA GTT AAC TTA ATC TTT GCA GAT         720
Glu Pro Lys Glu Glu Val Thr Ile Lys Val Asn Leu Ile Phe Ala Asp
225                 230                 235                 240
                                                    ┌─Z4
GGA AAA ACA CAA ACA GCA GAA TTC AAA GGA ACA TTT┌GAA GAA GCA ACA         768
Gly Lys Thr Gln Thr Ala Glu Phe Lys Gly Thr Phe Glu Glu Ala Thr
            245                 250                 255

GCA GAA GCT TAC AGA TAT GCA GAC TTA TTA GCA AAA GTA AAT GGT GAA         816
Ala Glu Ala Tyr Arg Tyr Ala Asp Leu Leu Ala Lys Val Asn Gly Glu
            260                 265                 270

TAC ACA GCA GAC TTA GAA GAT GGC GGA TAC ACT ATC AAC ATC AAA TTT         864
Tyr Thr Ala Asp Leu Glu Asp Gly Gly Tyr Thr Ile Asn Ile Lys Phe
            275                 280                 285

GCT GGA AAA TAA                                                         876
Ala Gly Lys  *
        290
```

*Fig. 2 CONTINUED*

IMMUNOGLOBULIN BINDING PROTEINS DERIVED FROM L PROTEIN AND THEIR USES

This application is a continuation of application Ser. No. 08/331,640, filed Nov. 7, 1994 now abandoned which is a 371 PCT/GB93/00950, filed May 7, 1993.

This invention relates to novel immunoglobulin binding proteins, processes for their production and recombinant DNA molecules coding therefor.

More specifically the present invention relates to synthetic proteins containing repeated sequences derived from selected binding regions of Protein L and to recombinant DNA molecules coding therefor.

A multitude of Gram-positive bacteria species have been isolated that express surface proteins with affinities for mammalian immunoglobulins through interaction with their heavy chains. The best known of these immunoglobulin binding proteins are type 1 Staphylococcus Protein A and type 2 Streptococcus Protein G which have been shown to interact principally through the C2–C3 interface on the Fc region of human immunoglobulins. In addition, both have also been shown to interact weakly to the Fab region, but again through the immunoglobulin heavy chain.

Recently, a novel protein from *Peptococcus magnus*, Protein L, has been reported that was found to bind to human, rabbit, porcine, mouse and rat immunoglobulins uniquely through interaction with their light chains. In humans this interaction has been shown to occur exclusively to the kappa chains. Since both kappa and lambda light chains are shared between different classes, Protein L binds strongly to all human classes, in particular to the multi-subunited IgM, and similarly is expected to bind to all classes in species that show Protein L light chain binding.

Both peptococcus and peptostreptococcus have been reported to produce Protein L, which binds to the Kappa light chain of human immunoglobulins. It has been proposed that Protein L is a virulence factor; non-virulent peptococci and peptostreptococci appear to neither express Protein L nor have the structural gene for it (Kastern et al 1990).

Protein L is of particular interest since it has been reported to bind to the Kappa light chain which is present in all classes and sub classes of immunoglobulins. As such it should prove to be a useful diagnostic reagent for use in ELISA and RIA techniques.

EP-A-0 255 497 describes the purification and attempted characterisation of Protein L by standard protein purification techniques. Subsequently, the authors of EP-A-0 255 497 have published a number of scientific papers describing further investigations into the nature and structure of Protein L, but to date, attempts fully to characterize the protein have failed. Thus recently, in a paper entitled "Protein L a Bacterial Immunoglobulin-Binding Protein and Possible Virulence Determinant" by W. Kastern et al (Infection and Immunity, May 1990, pp. 1217–1222) there are described unsuccessful attempts to isolate the gene coding for Protein L by determining N-terminal amino acid sequences of tryptic fragments of Protein L and using the derived sequence information to construct probes for isolating the gene. Although Protein L is useful for its immunoglobulin binding properties it is desirable to identify whether particular regions of Protein L confer immunoglobulin binding so that these regions may be used as the basis for construction of synthetic and improved immunoglobulin binding molecules. Due to lack of sequence information, it has hitherto not been possible to identify the Protein L sequences associated with complex formation with immunoglobulin Kappa light chains.

Hitherto, the problem of isolating and characterising the gene for Protein L has defined solution thereby preventing significant improvement in production of Protein L and preventing development of synthetic molecules derived from Protein L.

This invention is based on a cDNA sequence comprising a cDNA insert coding for Protein L in its entirety which has now been isolated, thus enabling the above problems to be solved. This cDNA sequence, and the amino acid sequence corresponding to the longest open reading frame thereof, are depicted in FIG. 1. The beginning of the signal sequence is marked as "SS" and the beginning of the mature protein is marked as "M". The longest open reading frame of the sequence depicted in FIG. 1 extends from TTG (103) to AAA (3183) and the depicted DNA comprises a coding region extending from nucleotide 208 to nucleotide 3183 which codes for immature Protein L.

The specific binding properties of Protein L, including its ability to bind immunoglobulin Kappa light chains, are believed to be attributable to the presence of sequences which have a reconizable repeated character within the amino acid sequence of the molecule.

By the term "recognizably repeated character" as used herein is meant that the amino acid sequence comprises at least two sequences, each of from 20 to 45 amino acids in length (or from 40 to 90 amino acids in length in the case of the D repeats), which have an at least 75%, preferably at least 90% and most preferably at least 95% homology with one another.

The polypeptide sequence depicted in FIG. 1 includes various sets of repeated sequences at least two of which are considered to be responsible for immunoglobulin Kappa light chain binding.

These sets of repeated sequences are labelled at their N-terminal ends as follows:

(1) A1, A2 and A3;
(2) B1 and B2;
(3) C1, C2, C3, and C4;
(4) Z1, Z2, Z3 and Z4;
(5) D1, D2, D3 and D4;

Each of the repeated sequences (1)–(4) has a length of between 25 and 45 amino acids. The ability to bind Kappa light chains is considered to be associated with one or more of the repeated sequences A, B, C and Z (sequences (1)–(4) above).

It is thus a feature of a first aspect of the invention to provide synthetic immunoglobulin binding molecules comprising a plurality of recognisably repeated binding domains selected from the sequences which are labelled at their N-terminal ends in FIG. 1 as A1, A2 and A3; B1, and B2; C1, C2, C3, and C4; and Z1, Z2, Z3 and Z4. The synthetic immunoglobulin binding molecules preferably comprise from 2 to 15 of said domains. The selected domain or domains may be identical to the sequences which are labelled at their N-terminal ends in FIG. 1 as A1, A2 and A3; B1, and B2; C1, C2, C3, and C4; Z1, Z2, Z3 and Z4, or they may vary from said sequences, provided that they have an at least 75%, preferably at least 90% and most preferably at least 95% homology therewith.

The sequences labelled at their N-terminal ends as D1, D2, D3 and D4 are believed to be resposible for albumin binding and the synthetic binding molecules provided according to the invention may include sequences selected from sequences D1, D2, D3 and D4 or related sequences which vary from said sequences, provided that they have an at least 75%, preferably at least 90% and most preferably at least 95% homology therewith.

In an embodiment of the invention hereinafter described a synthetic immunoglobulin binding molecule is provided in which domains C1 and Z1, and/or C2 and Z2 and/or C3 and Z3 and/or C4 and Z4 are present as binding region or regions. Region C1Z1 begins at the first amino acid of C1 and ends at the last amino acid of Z1, etc.

According to a further embodiment of the invention a synthetic immunoglobulin binding molecule comprises one or more immunoglobulin binding regions selected separately from:

(1) region C1Z1 of protein L, (2) region C2Z2 of protein L, (3) region C3Z3 of protein L, (4) region C4Z4 of protein L, and (5) a polypeptide sequence having at least 75% homology with one of the regions of (1), (2), (3) or (4) and substantially retaining the immunoglobulin binding activity of that region.

It is preferred that the synthetic molecule is substantially free of one or both of (1) protein L albumin binding activity and (2) protein L cell wall binding activity.

The sequence data shown in the figures indicate that regions C1Z1, C2Z2, C3Z3 and C4Z4 of protein L shown are respectively 71, 71, 74 and 75 amino acid residues in length. References in the invention to these regions are intended to encompass variants of these precise sequences. One such variant retains substantially the immunoglobulin binding activity of the precise sequence and has up to ten preferably up to 5 and very preferably no more than 2 amino acids substituted, added or deleted.

Another variant exhibits a degree of homology with one of the C1Z1, C2Z2, C3Z3 and C4Z4 sequences of 75% or more, preferably 90% or more while retaining substantially the immunoglobulin binding activity of the precise sequence.

The binding regions of the synthetic molecule are ligated directly to one another in one embodiment of the invention. In another embodiment binding regions are separated from each other by linker polypeptides, the nature of each linker being such as not to interfere with the binding activity of the binding domain. Linker polypeptides if present are preferably of up to 10 amino acids in length and most preferably up to 5 amino acids in length.

Although the invention includes synthetic molecules having a large number of binding regions it is convenient for the synthetic molecule to have from 1 to 4 such regions.

In a preferred embodiment of the invention the synthetic molecule has four such regions. The selection of a particular $C_n Z_n$ or $C_n Z_n$-derived variant sequence for each of the four regions is optional. Thus the synthetic molecules of the invention cover a large number of possible combinations of $C_n Z_n$ and $C_n Z_n$-derived variant sequences.

In a particular embodiment of the invention a synthetic molecule has four binding regions one each selected from C1Z1 or a variant thereof, C2Z2 or a variant thereof, C3Z3 or a variant thereof and C4Z4 or a variant thereof. An example of such an embodiment is shown in FIG. 2 which binds to immunoglobulin as native Protein L but does not bind to albumin or cell wall as native protein L.

The synthetic molecules of the invention can conveniently be used to form products for use in protein analysis, purification procedures and other biochemical processes according to methods well known in the art.

The synthetic immunoglobulin binding molecules can, for example, be ligated to a "reporter" molecule, such as an enzyme so as to be suitable for enzyme linked immunoabsorbent assay (ELISA). In another example to "reporter" molecule is suitable for use in a chemiluminescent assay.

The synthetic molecules of the invention can additionally be ligated to a molecule suitable for attachment to a solid support, such as a cysteine residue for attachment to a further cysteine residue on a solid matrix, or histidine for attachment to zinc on a support, or a mussel derived adhesive protein for attachment to a wide variety of surfaces including glass.

Thus the invention provides novel synthetic immunoglobulin binding molecules that are useful in a wide range of biochemical applications. The synthetic molecules are of particular advantage if they are free from regions D1, D2, D3 and D4 and as a result they do not exhibit the albumin binding and cell wall binding of native protein L. The synthetic molecules of the invention can conveniently be used to form products for use in protein analysis, purification procedures and other biochemical processes according to methods well known in the art.

According to a second aspect of the invention there is provided a recombinant DNA molecule containing an insert coding for a synthetic molecule according to any embodiment of the first aspect of the invention.

A nucleotide sequence of an embodiment of the second aspect of the invention is shown in FIG. 2.

It is straightforward for a man skilled in the art, once in possession of the DNA sequence coding for a desired polypeptide, to construct a vector capable of transforming a host cell so as to express that polypeptide.

Thus, according to a third aspect of the invention there is provided a process for producing a synthetic molecule of the first aspect of the invention comprising the steps of (a) transforming a host cell with an expression vector capable of transforming the host cell so as to express the synthetic molecule, (b) culturing the transformed host cell, and (c) isolating the synthetic molecule.

One such expression vector is plasmid pPPL2 described below and which has been deposited at NCIMB, Aberdeen, Scotland, UK under accession No. 40534 on Dec. 22, 1992.

BRIEF DESCRIPTION OF THE DRAWINGS

There now follows a description of exemplary embodiments of the invention in which:

FIG. 1 shows the nucleotide sequence of the gene coding for Protein L together with the amino acids coded for (SEQ ID NOS:1 and 2);

FIG. 2 shows the nucleotide sequence and the amino acid sequence coded thereby of an embodiment of the invention (SEQ ID NOS:3 and 4)

FIG. 3 shows 1.(a) Domain structure as determined by Kastern et al., Infect. Immunol., 58, 1992, and 1.(b) domain structure as determined by Murphy et al., Eur J. Biochem, 168, 1992. Shaded areas between the two figures represent areas of strong homology. To determine the domains responsible for the immunoglobulin-kappa binding reported for both molecules, and the albumin-binding reported for 1.(b), the deletion clones (constructed from the gene expressing 1.(b)) are shown in 2.(a,b,c).

EXAMPLE 1

Materials

Figure 3:
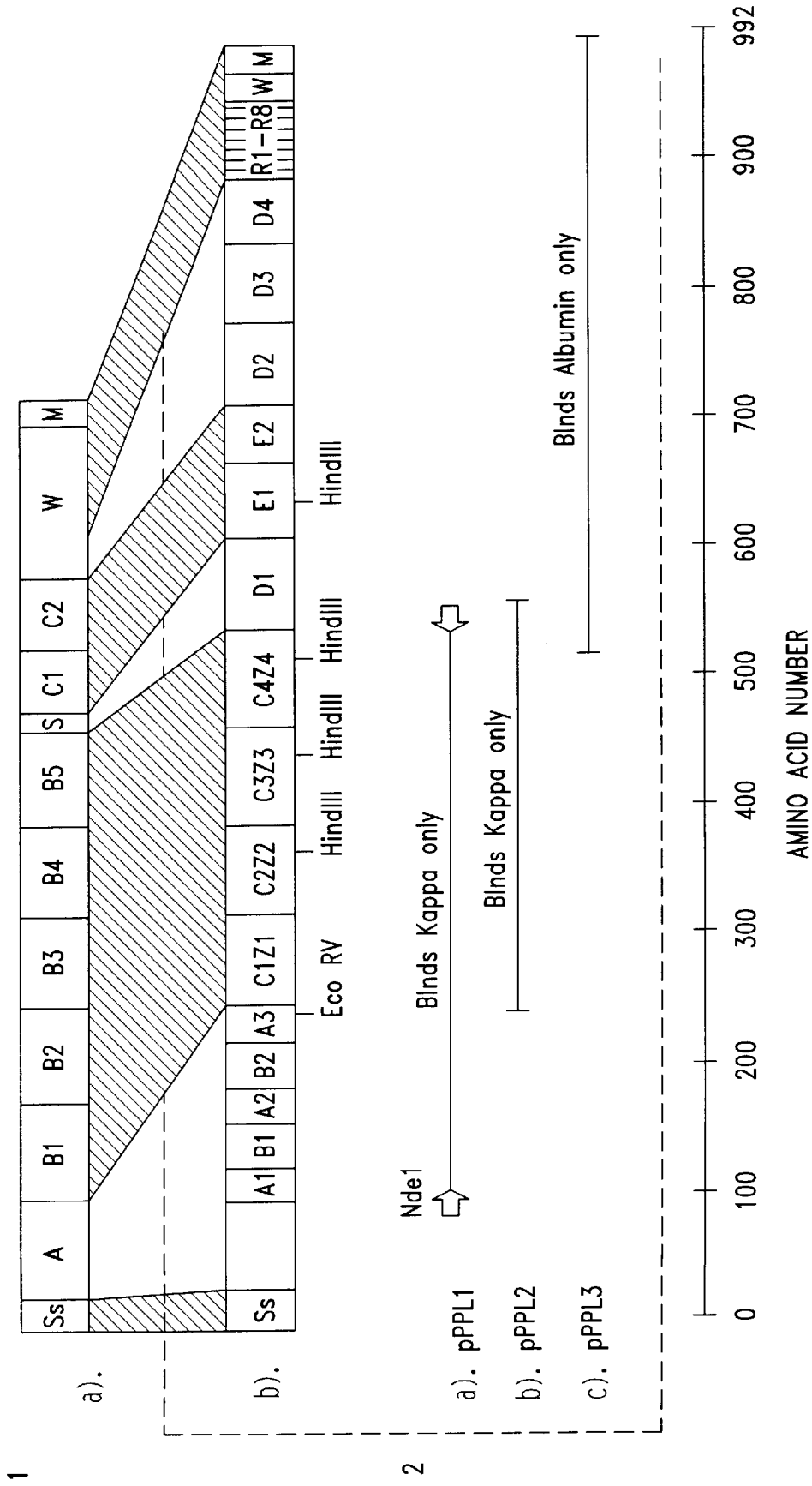
FIG. 3 shows a schematic representation of two different Protein L isolates and deletion clones constructed to determine the function of the separate binding domains.

X-Omat S X-ray film was from Kodak. DNA ligase, restriction endonucleases and other DNA-modifying enzymes were from Boehringer. Agarose, acrylamide, bis-acrylamide and phenol were from Bethesda Research Laboratories. Chromatography media was from Pharmacia LKB (Uppsala, Sweden). All immunoglobulins and serum albumin were from Sigma. All other reagents were from Sigma of BDH. Nunc 96 well microtitre plates were purchased from Gibco BRL Ltd.

Media and Cutlure Conditions

E. coli TG1 was cultured in 2xYT both (2% (w/v) tryptone/1% (w/v) yeast extract/1% (w/v) NaCl) overnight at 37° C. Media were solidified with 2% (w/v) Bacto-agar (Difco). Ampicillin (50 μg/ml) were used where necessary for the selection and growth of transformants. Functional β-galactosidase was detected by addition of chlorindolyl-β-D-galactoside to a final concentration of 600 μg/ml and, where necessary, isopropyl-β-D-thiogalactopyranoside to a final concentration of 200 μg/ml.

Isolation of DNA

Plasmid DNA was purified from E. coli by Brij lysis (Clewell and Helsinki, PNAS, U.S.A., 1969) and CsCl/ ethidium bromide density-gradient centrifugation (Radloff et al., PNAS, U.S.A. 1967).

Genetic Manipulation Procedures

DNA-modifying enzymes were used in the buffer and under the conditions recommended by the supplier (Boehringer). Transformation of E. coli was essentially as described previously (Cohen et al., PNAS, U.S.A. 1972). Electrophoresis of DNA fragments was performed on vertical 1% (w/v)-agarose slab gels in Tris-acetate buffer (40 mM-Tris/20 mM-sodium acetate/2 mM-EDTA, adjusted to pH 7.9 with acetic acid). DNA fragment sizes were estimated by comparison with fragments of lambda phage DNA previously digesed with the restriction endonuclease Hind III. DNA fragments were purified by electro-elution essentially as described previously (McDonnell et al., J. Mol. Biol., 100, 1977).

Constriction of Deletion Clones

A schematic representation of the deletion clones constructed are shown in FIG. 3.

pPPL1 was constructed by amplifying the DNA fragment indicated in FIG. 3 (2a) isolating the A, B, C and Z repeats. To facilitate expression, an Nde1 site (CAT ATG) was incorporated into the sense primer (5'-TTA AAT CAT ATG TCA GAA ACA-3') and to prevent read through, a stop condon was incorporated into the anti-sense primer (5'-CC TGG TTG TTA TTT TCC AGC AAA T-3'). This fragment was cloned into the TA cloning vector (Amersham), and subsequently excised on a Nde1-partial Hind III (cleaving at the Hind III site present in the TA cloning vectors polylinker) fragment, and re-cloned inframe into the Nde1-Hind III cleaved expression vector pMTL1013 (Brehm et al., Appl. Microbiol. Bitechnol., 36, 1991).

pPPL2, expressing only the C and Z repeats, was derived from pPPL1 by excision of the gene fragment shown in FIG. 3 (2b) through an Eco RV-Spe1 (site carried over from the TA cloning vector polylinker) digest, and re-cloned inframe into Sma1-Xba1 cleaved pMTL1013.

pPPL3 (FIG. 3 (2c)), expressing the D and E repeats, was obtained through a Pst1 (present upstream of the PPL open reading frame)-partial Hind III digest and cloned inframe into Hind III-Pst1 cleaved pMTL23 (Chambers et al., Gene. 68, 1988).

PCR

PCR was achieved by synthesising oligonucleotides (synthesised by solid phase synthesis using an Appied Biosystems Model 380A DNA synthesiser employing phosphoamidites) either side of the target site on the PPL gene and DNA fragments generated by the polymerase chain reaction using the method and reagents supplied in the PCR-Perking Elmer Cetus GeneAmp™ kit.

Sonication of Cells

A cell suspension was transferred to a MSE sonication tube and subjected to ultra sonication (3×30 sec bursts at 18 MHz with 30 sec intervals, at 4° C. using an MSE Soniprep 150 Sonicator).

Affinity Chromatography on IgG-Sepharose 4B

The sonication procedure was used to disrupt bacterial cells for small scale purification of immunoglobulin-binding proteins by affinity chromatography on IgG-sepharose FF. Cultures of 300 ml were grown overnight then centriguted (15000 g for 10 min at 4° C.) and resuspended in 3 ml of 100 mM Tris-HCl, pH 7.5. 250 mM NaCl. The suspension was sonicated, centrifuged (30000 g 10 min at 4° C.) and the supernatant fluid passed through a 1 ml column (1.6 cm×0.90 cm i.d.) of IgG-sepharose FF equilibrated and washed with 5 ml of 100 mM Tris-HCl, pH 7.5, 250 mM NaCl. The protein was eluted with 100 mM gylcine-HCl, pH 2.0, and the pH raised to 7.5 using 1M Tris, pH 8.0.

PAGE

Samples were solubilised under reducing condition and electrophoresis on SDS-polyacrylamide slab gels. Acrylamide (12.5% w/v) slab gels were run in an LKB vertical electrophoresis unit using the method of Laemmli (Laemmli, Nature, 227, 1970). Proteins were stained with Commassie Brilliant Blue R-250, and protein bands were scanned with a Chromoscan-3 laser optical densitometre (Joyce-Loebl, Gateshead, Tyne and Wear, U.K.), to estimate the apparent $M_r$.

Elisa Detecton Assay

Immunoglobulin-binding proteins were detected using an Elisa procedure modified from that previously described (Warenes et al., J. Immunol. Methods., 93, 1987).

Detection of Immunoglobulin-Binding

An aliquot of mouse IgG (100 μl) at 2.5 μg/ml in 50 mM sodium carbonate/bicarbonate buffer. pH9.6 was added to each well of a Maxisorp plate and the plate left overnight at 4° C. Following three washes with PBST-Phosphate buffered saline containing 0.05% (v/v) Tween 20, a 100 μl aliquot of the suspension of recombinant bacteria was transferred to the Maxisorp plate from overnight cultures. The immunoassay plate was then left at room temperature for an hour. After washing with PBST, 100 μl of human IgG at 1 μg/ml in PBST was added to each well and the plate left at room temperature for another hour. After a further wash, 100 μl of goat anti-human IgG (Fc specific) horseradish peroxidase conjugate (diluted 1:2000 in PBST was added to each well and the plate left at room temperature for a further hour. After further washing, 100 μl of reagent (60 μg/ml 3,3', 5,5'-Tetramethylbenzine dihydrochloride, 0.003% (v/v) hydrogen peroxide in 0.1M sodium acetate buffer, pH6.0) was added to each well and the reaction allowed to proceed for 10 min at room temperature. After this the reaction was stoped by the addition of 50 μl 11% (v/v) sulphuric acid to each well. The absorbance of the wells were then read at 450 nm against a reagent blank to measure the levels of immunoglobulin-binding proteins.

Detection of Albumin-Binding

To detect albumin-binding, the above procedure was followed except different affinity reagents were used in each step of the sandwich. The first step bound the protein sample under investigation, which has been prepared by recovering the cell supernatant following sonication, to the Maxisorp plate. Albumin-binding was then detected by incubating the plate with human serum albumin (HSA, 1 μg/ml) followed by goat-anti HSA IgG-horseradish peroxidase conjugated (1:2000 dilution), and then developed as above.

The Following Results Were Obtained pPPL1 and pPPL2 (FIG. 2 (2a,b)) were shown by Elisa to bind to IgG, lacking any albumin binding. pPPL3 (FIG. 2 (2c)) in contrast bound HSA, but not IgG. This shows that Kappa binding was through the C and Z repeats and that the albumin-binding was at a separate site located in the D- or E-repeats.

A purified solution of a synthetic immunoglobulin building molecule according to the invention can be obtained using the following method.

Host cells transformed with pPPL2 are grown, eg in a 400l to 4000l fermenter. The cell culture is then removed from the fermenter and spun down to obtain a cell paste, the supernatant culture medium being discarded.

The cell paste is washed in potassium phosphate buffer (pH 6.5) and lysosyme is added to lyse the cells over a suitable period of for example 30 to 60 minutes.

The lysed cells are next heated to 70° C. for 15 minutes and then centrifuged at 13000 rpm for 2 hours, leaving a supernatant of soluble, crude protein which is removed from the centrifuged pellet and can be stored at −20° C.

To obtain a sample of the synthetic molecule the crude protein, either thawed from store or direct from centrifuging is eluted through a Q-Sepharose column previously equilibrated with potassium phosphate buffer (pH 6.5). Before being added to the column the crude protein solution is diluted so as to be at the same ionic strength as the buffer.

The column is washed with buffer until no more protein is washed off, then washed with 50 mM NaCl solution to remove proteins binding weakly to the column. The strength of NaCl solution used to elute the column is then increased in steps and the protein fractions obtained kept separate.

The synthetic protein molecule of the invention is obtained from elution with NaCl between 270–290 mM.

The synthetic protein molecules of the invention, exemplified by that obtained as described above, find advantageous use in bio-assays and other biochemical applications due to their ability to bind to Kappa light chains of immunoglobulins. They are of use for example in ELISA, RIA, diagnosis, antibody purification.

FIG. 1 of GB 9209804.5 from which priority is claimed is reproduced as FIG. 1 of this application but with different nomenclature as set out below:

| GB 9209804.5 | This Application |
| --- | --- |
| A1, A2, A3 | A1, A2, A3 |
| B1, B2 | B1, B2 |
| C1, C2, C3, C4 | C1, C2, C3, C4 |
| D1, D2, D3, D4 | Z1, Z2, Z3, Z4 |
| E1, F1 | *D1 |
| E2, F2 | *D2 |
| E3, F3 | *D3 |
| E4, F4 | *D4 |

*The sequence now marked as D1 consists of the sequence originally marked E1 together with the sequence originally marked F1, etc.

This application uses the same nomenclature as the second priority application, GB 9226928.1.

We claim:

1. A synthetic molecule, comprising one or more immunoglobulin binding domain selected from the group consisting of the amino acid sequences a), b), c) and d) and sequences which have at least 95% homology with the sequences a), b), c) or d):

a)
Met Glu Thr Pro Glu Pro Glu Glu Glu Val Thr Ile Lys Ala Asn Leu Ile Phe Ala Asp Gly Ser Thr Gln Asn Ala Glu Phe Lys Gly Thr Phe Ala Lys Ala Val Ser Asp Ala Tyr Ala Tyr Ala Asp Ala Leu Lys Lys Asp Asn Gly Glu Tyr Thr Val Asp Val Ala Asp Lys Gly Leu Thr Leu Asn Ile Lys Phe Ala Gly Lys (SEQ ID NO:5)

b)
Lys Glu Lys Pro Glu Glu Pro Lys Glu Glu Val Thr Ile Lys Val Asn Leu Ile Phe Ala Asp Gly Lys Thr Gln Thr Ala Glu Phe Lys Gly Thr Phe Glu Glu Ala Thr Ala Lys Ala Tyr Ala Tyr Ala Asp Leu Leu Ala Lys Glu Asn Gly Glu Tyr Thr Ala Asp Leu Glu Asp Gly Gly Asn Thr Ile Asn Ile Lys Phe Ala Gly (SEQ ID NO:6)

c)
Lys Glu Thr Pro Glu Thr Pro Glu Glu Pro Lys Glu Glu Val Thr Ile Lys Val Asn Leu Ile Phe Ala Asp Gly Lys Ile Gln Thr Ala Glu Phe Lys Gly Thr Phe Glu Glu Ala Thr Ala Lys Ala Tyr Ala Tyr Ala Asn Leu Leu Ala Lys Glu Asn Gly Glu Tyr Thr Ala Asp Leu Glu Asp Gly Gly Asn Thr Ile Asn Ile Lys Phe Ala Gly (SEQ ID NO:7)

d)
Lys Glu Thr Pro Glu Thr Pro Glu Glu Pro Lys Glu Glu Val Thr Ile Lys Val Asn Leu Ile Phe Ala Asp Gly Lys Thr Gln Thr Ala Glu Phe Lys Gly Thr Phe Glu Glu Ala Thr Ala Glu Ala Tyr Arg Tyr Ala Asp Leu Leu Ala Lys Val Asn Gly Glu Tyr Thr Ala Asp Leu Glu Asp Gly Gly Tyr Thr Ile Asn Ile Lys Phe Ala Gly Lys (SEQ ID NO:8).

2. The synthetic molecule of claim 1 wherein the or each said domain is selected from the group consisting of the amino acid sequences a), b), c) and d).

3. The synthetic molecule of claim 1 consisting of one or more said domain selected from the group consisting of the amino acid sequences a), b), c) and d).

4. The synthetic molecule according to claim 1, further comprising one or more albumin binding domains selected from the group consisting of amino acid sequences D1), D2), D3) and D4):

D1)
Glu Gln Pro Gly Glu Asn Pro Gly Ile Thr Ile Asp Glu Trp Leu Leu Lys Asn Ala Lys Glu Glu Ala Ile Lys Glu Leu Lys Glu Ala Gly Ile Thr Ser Asp Leu Tyr Phe Ser Leu Ile Asn Lys Ala Lys Thr Val Glu Gly Val Glu Ala Leu Lys Asn Glu Ile Leu Lys Ala His Ala Gly Glu Glu Thr Pro Glu Leu Lys Asp Gly Tyr Ala Thr Tyr Glu Glu Ala Glu Ala Ala Ala Lys Glu Ala Leu Lys Asn Asp Val Asn Asn Ala Tyr Glu Ile Val Gln Gly Ala Asp Gly Arg Tyr Tyr Tyr Val Leu Lys Ile Glu Val Ala Asp Glu Glu Pro Gly Glu Asp Thr Pro Glu Val Gln Glu Gly Tyr Ala Thr Tyr Glu Glu Ala Glu Ala Ala Ala Lys Glu Ala Leu Lys Glu Asp Lys Val Asn Asn Ala Tyr Glu Val Val Gln Gly Ala Asp Gly Arg Tyr Tyr Tyr Val Leu Lys Ile Glu Asp Lys Glu Asp (SEQ ID NO:9)

D2)
Glu Gln Pro Gly Glu Pro Gly Glu Asn Pro Gly Ile Thr Ile Asp Glu Trp Leu Leu Lys Asn Ala Lys Glu Asp Ala Ile Lys Glu Leu Lys Glu Ala Gly Ile Ser Ser Asp Ile Tyr Phe Asp Ala Ile Asn Lys Ala Lys Thr Val Glu Gly Val Glu Ala Leu Lys Asn Glu Ile Leu Lys Ala His Ala (SEQ ID NO:10)

D3)
Glu Lys Pro Gly Glu Asn Pro Gly Ile Thr Ile Asp Glu Trp Leu Leu Lys Asn Ala Lys Glu Ala Ala Ile Lys Glu Leu Lys Glu Ala Gly Ile Thr Ala Glu Tyr Leu Phe Asn Leu Ile Asn Lys Ala Lys Thr Val Glu Gly Val Glu Ser Leu Lys Asn Glu Ile Leu Lys Ala His Ala (SEQ ID NO:11)

D4)
Glu Lys Pro Gly Glu Asn Pro Gly Ile Thr Ile Asp Glu Trp Leu Leu Lys Asn Ala Lys Glu Asp Ala Ile Lys Glu Leu Lys Glu Ala Gly Ile Thr Ser Asp Ile Tyr Phe Asp Ala Ile Asn Lys Ala Lys Thr Ile Glu Gly Val Glu Ala Leu Lys Asn Glu Ile Leu Lys Ala His (SEQ ID NO:12).

5. The synthetic molecule of claim 1 wherein said molecule does not bind albumin.

6. The synthetic molecule of claim 1 comprising a plurality of binding domains and further comprising one or more linker polypeptides of up to 10 amino acids wherein the or each linker polypeptide separates the binding domains from each other.

7. The synthetic molecule of claim 6 wherein the or each linker polypeptide is up to 5 amino acids in length.

8. The synthetic molecule of claim 1, further comprising a molecule for attachment to a solid support.

9. The synthetic molecule of claim 8 wherein said molecule for attachment to a solid support is selected from the group consisting of a cysteine residue, histidine and mussel derived adhesive protein.

* * * * *

UNITED STATES PATENT AND TRADEMARK OFFICE
CERTIFICATE OF CORRECTION

PATENT NO. : 6,162,903
DATED : December 19, 2000
INVENTOR(S) : Angus R. Trowern et al.

Page 1 of 1

It is certified that error appears in the above-identified patent and that said Letters Patent is hereby corrected as shown below:

<u>Title page,</u>
Item [56], References Cited,
The following FOREIGN PATENT DOCUMENT should appear as follows:
-- 93/22342    11/1993    (WO) --.

Signed and Sealed this

Twenty-fifth Day of December, 2001

*Attest:*

*Attesting Officer*

JAMES E. ROGAN
*Director of the United States Patent and Trademark Office*

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 3279 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (v) FRAGMENT TYPE: N-terminal (vi) ORIGINAL SOURCE:
      (A) ORGANISM: Peptostreptococcus asaccharolyticus
      (B) STRAIN: 1018

(ix) FEATURE:
      (A) NAME/KEY: exon
      (B) LOCATION: 103..3186
      (C) IDENTIFICATION METHOD: experimental
      (D) OTHER INFORMATION: /codon_start= 280
          /product= "mature protein L"
          /evidence= EXPERIMENTAL
          /number= 1

(ix) FEATURE:
      (A) NAME/KEY: CDS

-continued

```
        (B) LOCATION: 103..3186
        (D) OTHER INFORMATION: /codon_start= 103
               /product= "immature protein L"

(ix) FEATURE:
        (A) NAME/KEY: mat_peptide
        (B) LOCATION: 280..3183
        (D) OTHER INFORMATION: /codon_start= 280
               /product= "mature protein L"

(ix) FEATURE:
        (A) NAME/KEY: misc_signal
        (B) LOCATION: 208..279

(xi) SEQUENCE DESCRIPTION: SEQ ID NO:1:
```

| | | |
|---|---|---|
| TTTGGACAGT GGACGAAACA AGAACACTGA TTTAATAAAT TGGTGAAATT CGATTGTTGA | | 60 |
| AATACCTTTT TGGGTAGAAA TAACTAAGGA ATGGCAATAT AA TTG CTT GGA AAC<br>                                         Leu Leu Gly Asn<br>                                          -59 | | 114 |
| GAA TTT GAT TTA AAT AGC ATT AAA TGC AAA AAA TTT AAA AGG AGG AGA<br>Glu Phe Asp Leu Asn Ser Ile Lys Cys Lys Lys Phe Lys Arg Arg Arg<br>-55             -50                 -45                 -40 | | 162 |
| CAA ATT CCA CCC TTT ATA AAG GGA AGT TTC CAT TGT CAA AAT AAT ATG<br>Gln Ile Pro Pro Phe Ile Lys Gly Ser Phe His Cys Gln Asn Asn Met<br>                 -35                 -30                 -25 | | 210 |
| AAG ATT AAT AAG AAA TTA TTA ATG GCT GCA CTT GCA GGA GCA ATT GTA<br>Lys Ile Asn Lys Lys Leu Leu Met Ala Ala Leu Ala Gly Ala Ile Val<br>             -20                 -15                 -10 | | 258 |
| GTT GGT GGT GGA GCT AAC GCT TAC GCA GCT GAA GAA GAT AAC ACT GAT<br>Val Gly Gly Gly Ala Asn Ala Tyr Ala Ala Glu Glu Asp Asn Thr Asp<br>     -5                   1                   5 | | 306 |
| AAT AAC CTT TCA ATG GAT GAA ATT AGT GAT GCT TAT TTT GAT TAT CAC<br>Asn Asn Leu Ser Met Asp Glu Ile Ser Asp Ala Tyr Phe Asp Tyr His<br>10                  15                  20                  25 | | 354 |
| GGA GAT GTT TCA GAT TCA GTA GAT CCT GTA GAA GAA GAA ATA GAC GAA<br>Gly Asp Val Ser Asp Ser Val Asp Pro Val Glu Glu Glu Ile Asp Glu<br>                 30                  35                  40 | | 402 |
| GCA TTA GCA AAA GCA TTA GCA GAA GCT AAA GAA ACA GCA AAA AAA CAT<br>Ala Leu Ala Lys Ala Leu Ala Glu Ala Lys Glu Thr Ala Lys Lys His<br>             45                  50                  55 | | 450 |
| ATA GAT TCT TTA AAT CAT TTG TCA GAA ACA GCA AAA AAA TTA GCT AAG<br>Ile Asp Ser Leu Asn His Leu Ser Glu Thr Ala Lys Lys Leu Ala Lys<br>         60                  65                  70 | | 498 |
| AAT GAT ATA GAT TCA GCT ACT ACT ATT AAT GCA ATC AAT GAC ATC GTA<br>Asn Asp Ile Asp Ser Ala Thr Thr Ile Asn Ala Ile Asn Asp Ile Val<br>     75                  80                  85 | | 546 |
| GCA AGA GCA GAT GTA ATG GAA AGA AAA ACA GCT GAA AAA GAA GAA GCA<br>Ala Arg Ala Asp Val Met Glu Arg Lys Thr Ala Glu Lys Glu Glu Ala<br>90                  95                 100                 105 | | 594 |
| GAA AAA TTA GCA GCA GCA AAA GAA ACA GCA AAG AAA CAT ATA GAT GAA<br>Glu Lys Leu Ala Ala Ala Lys Glu Thr Ala Lys Lys His Ile Asp Glu<br>                 110                 115                 120 | | 642 |
| TTA AAA CAC TTA GCA GAC AAA ACA AAA GAA TTA GCT AAG AGA GAT ATA<br>Leu Lys His Leu Ala Asp Lys Thr Lys Glu Leu Ala Lys Arg Asp Ile<br>             125                 130                 135 | | 690 |
| GAT TCA GCT ACT ACT ATT AAT GCA ATC AAT GAC ATC GTA GCA AGA GCA<br>Asp Ser Ala Thr Thr Ile Asn Ala Ile Asn Asp Ile Val Ala Arg Ala<br>         140                 145                 150 | | 738 |
| GAT GTA ATG GAA AGA AAA ACA GCT GAA AAA GAA GAA GCA GAA AAA TTA<br>Asp Val Met Glu Arg Lys Thr Ala Glu Lys Glu Glu Ala Glu Lys Leu<br>     155                 160                 165 | | 786 |
| GCA GCA GCA AAA GAA ACA GCA AAG AAA CAT ATA GAT GAA TTA AAA CAC | | 834 |

-continued

| | | | | | | | | | | | | | | |
|---|---|---|---|---|---|---|---|---|---|---|---|---|---|---|
| Ala | Ala | Ala | Lys | Glu | Thr | Ala | Lys | Lys | His | Ile | Asp | Glu | Leu | Lys | His |
| 170 | | | | 175 | | | | | 180 | | | | | 185 | |

| TTA | GCA | GAC | AAA | ACA | AAA | GAA | TTA | GCT | AAG | AGA | GAT | ATA | GAT | TCA | GCT | 882 |
|---|---|---|---|---|---|---|---|---|---|---|---|---|---|---|---|---|
| Leu | Ala | Asp | Lys | Thr | Lys | Glu | Leu | Ala | Lys | Arg | Asp | Ile | Asp | Ser | Ala | |
| | | | | 190 | | | | | 195 | | | | | 200 | | |

| ACT | ACT | ATT | GAT | GCA | ATC | AAT | GAT | ATC | GTA | GCT | AGA | GCA | GAT | GTA | ATG | 930 |
|---|---|---|---|---|---|---|---|---|---|---|---|---|---|---|---|---|
| Thr | Thr | Ile | Asp | Ala | Ile | Asn | Asp | Ile | Val | Ala | Arg | Ala | Asp | Val | Met | |
| | | | | 205 | | | | | 210 | | | | | 215 | | |

| GAA | AGA | AAG | TTA | TCT | GAA | AAA | GAA | ACA | CCA | GAA | CCA | GAA | GAA | GAA | GTT | 978 |
|---|---|---|---|---|---|---|---|---|---|---|---|---|---|---|---|---|
| Glu | Arg | Lys | Leu | Ser | Glu | Lys | Glu | Thr | Pro | Glu | Pro | Glu | Glu | Glu | Val | |
| | | | 220 | | | | | 225 | | | | | 230 | | | |

| ACA | ATC | AAA | GCT | AAC | TTA | ATC | TTT | GCA | GAT | GGA | AGC | ACA | CAA | AAT | GCA | 1026 |
|---|---|---|---|---|---|---|---|---|---|---|---|---|---|---|---|---|
| Thr | Ile | Lys | Ala | Asn | Leu | Ile | Phe | Ala | Asp | Gly | Ser | Thr | Gln | Asn | Ala | |
| | | 235 | | | | | 240 | | | | | 245 | | | | |

| GAA | TTC | AAA | GGA | ACA | TTC | GCA | AAA | GCA | GTA | TCA | GAT | GCT | TAC | GCT | TAC | 1074 |
|---|---|---|---|---|---|---|---|---|---|---|---|---|---|---|---|---|
| Glu | Phe | Lys | Gly | Thr | Phe | Ala | Lys | Ala | Val | Ser | Asp | Ala | Tyr | Ala | Tyr | |
| 250 | | | | | 255 | | | | | 260 | | | | | 265 | |

| GCA | GAT | GCT | TTA | AAG | AAA | GAC | AAC | GGA | GAA | TAT | ACT | GTA | GAC | GTT | GCA | 1122 |
|---|---|---|---|---|---|---|---|---|---|---|---|---|---|---|---|---|
| Ala | Asp | Ala | Leu | Lys | Lys | Asp | Asn | Gly | Glu | Tyr | Thr | Val | Asp | Val | Ala | |
| | | | | 270 | | | | | 275 | | | | | 280 | | |

| GAT | AAA | GGC | TTA | ACT | TTA | AAT | ATT | AAA | TTC | GCT | GGT | AAA | AAA | GAA | AAA | 1170 |
|---|---|---|---|---|---|---|---|---|---|---|---|---|---|---|---|---|
| Asp | Lys | Gly | Leu | Thr | Leu | Asn | Ile | Lys | Phe | Ala | Gly | Lys | Lys | Glu | Lys | |
| | | | 285 | | | | | 290 | | | | | 295 | | | |

| CCA | GAA | GAA | CCA | AAA | GAA | GAA | GTT | ACA | ATC | AAA | GTT | AAC | TTA | ATC | TTT | 1218 |
|---|---|---|---|---|---|---|---|---|---|---|---|---|---|---|---|---|
| Pro | Glu | Glu | Pro | Lys | Glu | Glu | Val | Thr | Ile | Lys | Val | Asn | Leu | Ile | Phe | |
| | | 300 | | | | | 305 | | | | | 310 | | | | |

| GCA | GAT | GGA | AAG | ACA | CAA | ACA | GCA | GAA | TTC | AAA | GGA | ACA | TTT | GAA | GAA | 1266 |
|---|---|---|---|---|---|---|---|---|---|---|---|---|---|---|---|---|
| Ala | Asp | Gly | Lys | Thr | Gln | Thr | Ala | Glu | Phe | Lys | Gly | Thr | Phe | Glu | Glu | |
| | | 315 | | | | | 320 | | | | | 325 | | | | |

| GCA | ACA | GCA | AAA | GCT | TAT | GCT | TAT | GCA | GAC | TTA | TTA | GCA | AAA | GAA | AAT | 1314 |
|---|---|---|---|---|---|---|---|---|---|---|---|---|---|---|---|---|
| Ala | Thr | Ala | Lys | Ala | Tyr | Ala | Tyr | Ala | Asp | Leu | Leu | Ala | Lys | Glu | Asn | |
| 330 | | | | | 335 | | | | | 340 | | | | | 345 | |

| GGC | GAA | TAT | ACA | GCA | GAC | TTA | GAA | GAT | GGT | GGA | AAC | ACA | ATC | AAC | ATT | 1362 |
|---|---|---|---|---|---|---|---|---|---|---|---|---|---|---|---|---|
| Gly | Glu | Tyr | Thr | Ala | Asp | Leu | Glu | Asp | Gly | Gly | Asn | Thr | Ile | Asn | Ile | |
| | | | | 350 | | | | | 355 | | | | | 360 | | |

| AAA | TTT | GCT | GGA | AAA | GAA | ACA | CCA | GAA | ACA | CCA | GAA | GAA | CCA | AAA | GAA | 1410 |
|---|---|---|---|---|---|---|---|---|---|---|---|---|---|---|---|---|
| Lys | Phe | Ala | Gly | Lys | Glu | Thr | Pro | Glu | Thr | Pro | Glu | Glu | Pro | Lys | Glu | |
| | | | 365 | | | | | 370 | | | | | 375 | | | |

| GAA | GTT | ACA | ATC | AAA | GTT | AAC | TTA | ATC | TTT | GCA | GAT | GGA | AAG | ATA | CAA | 1458 |
|---|---|---|---|---|---|---|---|---|---|---|---|---|---|---|---|---|
| Glu | Val | Thr | Ile | Lys | Val | Asn | Leu | Ile | Phe | Ala | Asp | Gly | Lys | Ile | Gln | |
| | | | 380 | | | | | 385 | | | | | 390 | | | |

| ACA | GCA | GAA | TTC | AAA | GGA | ACA | TTT | GAA | GAA | GCA | ACA | GCA | AAA | GCT | TAT | 1506 |
|---|---|---|---|---|---|---|---|---|---|---|---|---|---|---|---|---|
| Thr | Ala | Glu | Phe | Lys | Gly | Thr | Phe | Glu | Glu | Ala | Thr | Ala | Lys | Ala | Tyr | |
| | 395 | | | | | 400 | | | | | 405 | | | | | |

| GCT | TAT | GCA | AAC | TTA | TTA | GCA | AAA | GAA | AAT | GGC | GAA | TAT | ACA | GCA | GAC | 1554 |
|---|---|---|---|---|---|---|---|---|---|---|---|---|---|---|---|---|
| Ala | Tyr | Ala | Asn | Leu | Leu | Ala | Lys | Glu | Asn | Gly | Glu | Tyr | Thr | Ala | Asp | |
| 410 | | | | | 415 | | | | | 420 | | | | | 425 | |

| TTA | GAA | GAT | GGT | GGA | AAC | ACA | ATC | AAC | ATT | AAA | TTT | GCT | GGA | AAA | GAA | 1602 |
|---|---|---|---|---|---|---|---|---|---|---|---|---|---|---|---|---|
| Leu | Glu | Asp | Gly | Gly | Asn | Thr | Ile | Asn | Ile | Lys | Phe | Ala | Gly | Lys | Glu | |
| | | | | 430 | | | | | 435 | | | | | 440 | | |

| ACA | CCA | GAA | ACA | CCA | GAA | GAA | CCA | AAA | GAA | GAA | GTT | ACA | ATC | AAA | GTT | 1650 |
|---|---|---|---|---|---|---|---|---|---|---|---|---|---|---|---|---|
| Thr | Pro | Glu | Thr | Pro | Glu | Glu | Pro | Lys | Glu | Glu | Val | Thr | Ile | Lys | Val | |
| | | | 445 | | | | | 450 | | | | | 455 | | | |

| AAC | TTA | ATC | TTT | GCA | GAT | GGA | AAA | ACA | CAA | ACA | GCA | GAA | TTC | AAA | GGA | 1698 |
|---|---|---|---|---|---|---|---|---|---|---|---|---|---|---|---|---|
| Asn | Leu | Ile | Phe | Ala | Asp | Gly | Lys | Thr | Gln | Thr | Ala | Glu | Phe | Lys | Gly | |
| | | | 460 | | | | | 465 | | | | | 470 | | | |

| ACA | TTT | GAA | GAA | GCA | ACA | GCA | GAA | GCT | TAC | AGA | TAT | GCA | GAC | TTA | TTA | 1746 |
|---|---|---|---|---|---|---|---|---|---|---|---|---|---|---|---|---|
| Thr | Phe | Glu | Glu | Ala | Thr | Ala | Glu | Ala | Tyr | Arg | Tyr | Ala | Asp | Leu | Leu | |
| | | 475 | | | | | 480 | | | | | 485 | | | | |

```
GCA AAA GTA AAT GGT GAA TAC ACA GCA GAC TTA GAA GAT GGC GGA TAC        1794
Ala Lys Val Asn Gly Glu Tyr Thr Ala Asp Leu Glu Asp Gly Gly Tyr
490                 495                 500                 505

ACT ATC AAC ATC AAA TTT GCT GGA AAA GAA CAA CCA GGC GAA AAT CCA        1842
Thr Ile Asn Ile Lys Phe Ala Gly Lys Glu Gln Pro Gly Glu Asn Pro
                510                 515                 520

GGA ATC ACA ATT GAT GAA TGG TTA TTA AAG AAT GCT AAA GAA GAA GCA        1890
Gly Ile Thr Ile Asp Glu Trp Leu Leu Lys Asn Ala Lys Glu Glu Ala
                525                 530                 535

ATC AAA GAA TTA AAA GAA GCA GGA ATC ACT TCT GAT TTA TAC TTC AGC        1938
Ile Lys Glu Leu Lys Glu Ala Gly Ile Thr Ser Asp Leu Tyr Phe Ser
            540                 545                 550

TTA ATC AAT AAA GCA AAA ACA GTT GAA GGC GTA GAA GCA TTA AAG AAC        1986
Leu Ile Asn Lys Ala Lys Thr Val Glu Gly Val Glu Ala Leu Lys Asn
        555                 560                 565

GAA ATC TTA AAA GCA CAC GCT GGA GAA GAA ACA CCA GAA TTA AAA GAT        2034
Glu Ile Leu Lys Ala His Ala Gly Glu Glu Thr Pro Glu Leu Lys Asp
570                 575                 580                 585

GGA TAT GCA ACA TAT GAA GAA GCA GAA GCA GCA AAA GAA GCT TTG            2082
Gly Tyr Ala Thr Tyr Glu Glu Ala Glu Ala Ala Lys Glu Ala Leu
                590                 595                 600

AAA AAT GAT GAT GTT AAC AAC GCA TAC GAA ATA GTT CAA GGT GCA GAC        2130
Lys Asn Asp Asp Val Asn Asn Ala Tyr Glu Ile Val Gln Gly Ala Asp
                605                 610                 615

GGA AGA TAC TAC TAT GTA TTA AAG ATT GAA GTT GCA GAC GAA GAA GAA        2178
Gly Arg Tyr Tyr Tyr Val Leu Lys Ile Glu Val Ala Asp Glu Glu Glu
            620                 625                 630

CCA GGT GAA GAC ACT CCA GAA GTT CAA GAA GGT TAC GCA ACT TAC GAA        2226
Pro Gly Glu Asp Thr Pro Glu Val Gln Glu Gly Tyr Ala Thr Tyr Glu
        635                 640                 645

GAA GCA GAA GCA GCA GCT AAA GAA GCA TTA AAA GAA GAT AAA GTT AAC        2274
Glu Ala Glu Ala Ala Ala Lys Glu Ala Leu Lys Glu Asp Lys Val Asn
650                 655                 660                 665

AAT GCA TAC GAA GTA GTT CAA GGT GCA GAC GGA AGA TAC TAC TAT GTA        2322
Asn Ala Tyr Glu Val Val Gln Gly Ala Asp Gly Arg Tyr Tyr Tyr Val
                670                 675                 680

TTA AAA ATC GAA GAT AAA GAA GAT GAA CAA CCA GGT GAA GAA CCA GGC        2370
Leu Lys Ile Glu Asp Lys Glu Asp Glu Gln Pro Gly Glu Glu Pro Gly
                685                 690                 695

GAA AAC CCA GGA ATC ACA ATT GAT GAA TGG TTA TTA AAG AAT GCT AAA        2418
Glu Asn Pro Gly Ile Thr Ile Asp Glu Trp Leu Leu Lys Asn Ala Lys
            700                 705                 710

GAA GAC GCA ATC AAA GAA TTA AAA GAA GCA GGA ATC AGT TCT GAC ATA        2466
Glu Asp Ala Ile Lys Glu Leu Lys Glu Ala Gly Ile Ser Ser Asp Ile
        715                 720                 725

TAC TTT GAT GCA ATC AAC AAA GCA AAA ACA GTA GAA GGC GTA GAA GCG        2514
Tyr Phe Asp Ala Ile Asn Lys Ala Lys Thr Val Glu Gly Val Glu Ala
730                 735                 740                 745

TTA AAG AAC GAA ATC TTA AAA GCA CAC GCT GAA AAA CCA GGC GAA AAC        2562
Leu Lys Asn Glu Ile Leu Lys Ala His Ala Glu Lys Pro Gly Glu Asn
                750                 755                 760

CCA GGA ATC ACA ATT GAT GAA TGG TTA TTA AAG AAT GCT AAA GAA GCT        2610
Pro Gly Ile Thr Ile Asp Glu Trp Leu Leu Lys Asn Ala Lys Glu Ala
                765                 770                 775

GCA ATC AAA GAA TTA AAA GAA GCA GGA ATC ACT GCT GAA TAT CTA TTC        2658
Ala Ile Lys Glu Leu Lys Glu Ala Gly Ile Thr Ala Glu Tyr Leu Phe
            780                 785                 790

AAC TTA ATC AAC AAA GCA AAA ACA GTA GAA GGC GTA GAA TCA TTA AAG        2706
Asn Leu Ile Asn Lys Ala Lys Thr Val Glu Gly Val Glu Ser Leu Lys
        795                 800                 805
```

-continued

```
AAC GAA ATC TTA AAA GCA CAC GCT GAA AAA CCA GGC GAA AAC CCA GGA    2754
Asn Glu Ile Leu Lys Ala His Ala Glu Lys Pro Gly Glu Asn Pro Gly
810             815                 820                 825

ATC ACA ATT GAT GAA TGG TTA TTA AAG AAC GCT AAA GAA GAT GCA ATT    2802
Ile Thr Ile Asp Glu Trp Leu Leu Lys Asn Ala Lys Glu Asp Ala Ile
                830                 835                 840

AAA GAA TTA AAA GAA GCA GGA ATT ACT TCT GAC ATA TAC TTT GAT GCT    2850
Lys Glu Leu Lys Glu Ala Gly Ile Thr Ser Asp Ile Tyr Phe Asp Ala
            845                 850                 855

ATC AAC AAA GCA AAA ACT ATT GAA GGC GTA GAA GCA TTA AAG AAT GAA    2898
Ile Asn Lys Ala Lys Thr Ile Glu Gly Val Glu Ala Leu Lys Asn Glu
        860                 865                 870

ATC TTA AAG GCT CAT AAA AAA GAT GAA GAA CCA GGT AAA AAA CCA GGT    2946
Ile Leu Lys Ala His Lys Lys Asp Glu Glu Pro Gly Lys Lys Pro Gly
    875                 880                 885

GAA GAC AAA AAA CCA GAA GAT AAA AAA CCA GGT GAA GAT AAA AAA CCA    2994
Glu Asp Lys Lys Pro Glu Asp Lys Lys Pro Gly Glu Asp Lys Lys Pro
890                 895                 900                 905

GAA GAC AAA AAA CCT GGT GAA GAT AAA AAA CCA GAA GAC AAA AAA CCA    3042
Glu Asp Lys Lys Pro Gly Glu Asp Lys Lys Pro Glu Asp Lys Lys Pro
                910                 915                 920

GGT AAA ACA GAT AAA GAT TCT CCA AAT AAG AAG AAA AAA GCT AAA TTA    3090
Gly Lys Thr Asp Lys Asp Ser Pro Asn Lys Lys Lys Lys Ala Lys Leu
            925                 930                 935

CCA AAA GCT GGT AGC GAA GCT GAA ATC TTA ACA TTA GCA GCA GCA GCT    3138
Pro Lys Ala Gly Ser Glu Ala Glu Ile Leu Thr Leu Ala Ala Ala Ala
        940                 945                 950

TTA TCA ACA GCA GCA GGT GCT TAC GTT TCA CTT AAA AAA CCT AAA TAA    3186
Leu Ser Thr Ala Ala Gly Ala Tyr Val Ser Leu Lys Lys Pro Lys
    955                 960                 965

TTAATCTTAG ATAAAGAATA GATTAATATA AAAAATGGGA CTTATAATAG TCCCATTTTT  3246

TAATGCGAAA AACTGATACA AAAAATGTAT CAG                                3279

(2) INFORMATION FOR SEQ ID NO:2:

(i) SEQUENCE CHARACTERISTICS:
        (A) LENGTH: 1027 amino acids
        (B) TYPE: amino acid
        (D) TOPOLOGY: linear (ii) MOLECULE TYPE: protein (xi) SEQUENCE DESCRIPTION: SEQ ID NO:2:

Leu Leu Gly Asn Glu Phe Asp Leu Asn Ser Ile Lys Cys Lys Lys Phe
-59             -55                 -50                 -45

Lys Arg Arg Arg Gln Ile Pro Pro Phe Ile Lys Gly Ser Phe His Cys
            -40                 -35                 -30

Gln Asn Asn Met Lys Ile Asn Lys Lys Leu Leu Met Ala Ala Leu Ala
        -25                 -20                 -15

Gly Ala Ile Val Val Gly Gly Gly Ala Asn Ala Tyr Ala Ala Glu Glu
    -10                 -5                   1                   5

Asp Asn Thr Asp Asn Asn Leu Ser Met Asp Glu Ile Ser Asp Ala Tyr
                10                  15                  20

Phe Asp Tyr His Gly Asp Val Ser Asp Ser Val Asp Pro Val Glu Glu
            25                  30                  35

Glu Ile Asp Glu Ala Leu Ala Lys Ala Leu Ala Glu Ala Lys Glu Thr
        40                  45                  50

Ala Lys Lys His Ile Asp Ser Leu Asn His Leu Ser Glu Thr Ala Lys
```

-continued

```
                55                  60                  65
Lys Leu Ala Lys Asn Asp Ile Asp Ser Ala Thr Thr Ile Asn Ala Ile
70                  75                  80                  85
Asn Asp Ile Val Ala Arg Ala Asp Val Met Glu Arg Lys Thr Ala Glu
                90                  95                 100
Lys Glu Glu Ala Glu Lys Leu Ala Ala Ala Lys Glu Thr Ala Lys Lys
               105                 110                 115
His Ile Asp Glu Leu Lys His Leu Ala Asp Lys Thr Lys Glu Leu Ala
               120                 125                 130
Lys Arg Asp Ile Asp Ser Ala Thr Thr Ile Asn Ala Ile Asn Asp Ile
               135                 140                 145
Val Ala Arg Ala Asp Val Met Glu Arg Lys Thr Ala Glu Lys Glu Glu
150                 155                 160                 165
Ala Glu Lys Leu Ala Ala Ala Lys Glu Thr Ala Lys Lys His Ile Asp
                   170                 175                 180
Glu Leu Lys His Leu Ala Asp Lys Thr Lys Glu Leu Ala Lys Arg Asp
                   185                 190                 195
Ile Asp Ser Ala Thr Thr Ile Asp Ala Ile Asn Asp Ile Val Ala Arg
               200                 205                 210
Ala Asp Val Met Glu Arg Lys Leu Ser Glu Lys Glu Thr Pro Glu Pro
215                 220                 225
Glu Glu Glu Val Thr Ile Lys Ala Asn Leu Ile Phe Ala Asp Gly Ser
230                 235                 240                 245
Thr Gln Asn Ala Glu Phe Lys Gly Thr Phe Ala Lys Ala Val Ser Asp
               250                 255                 260
Ala Tyr Ala Tyr Ala Asp Ala Leu Lys Lys Asp Asn Gly Glu Tyr Thr
               265                 270                 275
Val Asp Val Ala Asp Lys Gly Leu Thr Leu Asn Ile Lys Phe Ala Gly
               280                 285                 290
Lys Lys Glu Lys Pro Glu Glu Pro Lys Glu Glu Val Thr Ile Lys Val
               295                 300                 305
Asn Leu Ile Phe Ala Asp Gly Lys Thr Gln Thr Ala Glu Phe Lys Gly
310                 315                 320                 325
Thr Phe Glu Glu Ala Thr Ala Lys Ala Tyr Ala Tyr Ala Asp Leu Leu
                   330                 335                 340
Ala Lys Glu Asn Gly Glu Tyr Thr Ala Asp Leu Glu Asp Gly Gly Asn
               345                 350                 355
Thr Ile Asn Ile Lys Phe Ala Gly Lys Glu Thr Pro Glu Thr Pro Glu
               360                 365                 370
Glu Pro Lys Glu Glu Val Thr Ile Lys Val Asn Leu Ile Phe Ala Asp
               375                 380                 385
Gly Lys Ile Gln Thr Ala Glu Phe Lys Gly Thr Phe Glu Glu Ala Thr
390                 395                 400                 405
Ala Lys Ala Tyr Ala Tyr Ala Asn Leu Leu Ala Lys Glu Asn Gly Glu
                   410                 415                 420
Tyr Thr Ala Asp Leu Glu Asp Gly Gly Asn Thr Ile Asn Ile Lys Phe
               425                 430                 435
Ala Gly Lys Glu Thr Pro Glu Thr Pro Glu Glu Pro Lys Glu Glu Val
               440                 445                 450
Thr Ile Lys Val Asn Leu Ile Phe Ala Asp Gly Lys Thr Gln Thr Ala
               455                 460                 465
Glu Phe Lys Gly Thr Phe Glu Glu Ala Thr Ala Glu Ala Tyr Arg Tyr
470                 475                 480                 485
```

-continued

```
Ala Asp Leu Leu Ala Lys Val Asn Gly Glu Tyr Thr Ala Asp Leu Glu
                490                 495                 500

Asp Gly Gly Tyr Thr Ile Asn Ile Lys Phe Ala Gly Lys Glu Gln Pro
            505                 510                 515

Gly Glu Asn Pro Gly Ile Thr Ile Asp Glu Trp Leu Leu Lys Asn Ala
            520                 525                 530

Lys Glu Glu Ala Ile Lys Glu Leu Lys Glu Ala Gly Ile Thr Ser Asp
            535                 540                 545

Leu Tyr Phe Ser Leu Ile Asn Lys Ala Lys Thr Val Glu Gly Val Glu
550                 555                 560                 565

Ala Leu Lys Asn Glu Ile Leu Lys Ala His Ala Gly Glu Glu Thr Pro
                570                 575                 580

Glu Leu Lys Asp Gly Tyr Ala Thr Tyr Glu Glu Ala Glu Ala Ala Ala
                585                 590                 595

Lys Glu Ala Leu Lys Asn Asp Val Asn Asn Ala Tyr Glu Ile Val
                600                 605                 610

Gln Gly Ala Asp Gly Arg Tyr Tyr Val Leu Lys Ile Glu Val Ala
                615                 620                 625

Asp Glu Glu Glu Pro Gly Glu Asp Thr Pro Glu Val Gln Glu Gly Tyr
630                 635                 640                 645

Ala Thr Tyr Glu Glu Ala Glu Ala Ala Ala Lys Glu Ala Leu Lys Glu
                650                 655                 660

Asp Lys Val Asn Asn Ala Tyr Glu Val Val Gln Gly Ala Asp Gly Arg
                665                 670                 675

Tyr Tyr Tyr Val Leu Lys Ile Glu Asp Lys Glu Asp Glu Gln Pro Gly
                680                 685                 690

Glu Glu Pro Gly Glu Asn Pro Gly Ile Thr Ile Asp Glu Trp Leu Leu
                695                 700                 705

Lys Asn Ala Lys Glu Asp Ala Ile Lys Glu Leu Lys Glu Ala Gly Ile
710                 715                 720                 725

Ser Ser Asp Ile Tyr Phe Asp Ala Ile Asn Lys Ala Lys Thr Val Glu
                730                 735                 740

Gly Val Glu Ala Leu Lys Asn Glu Ile Leu Lys Ala His Ala Glu Lys
                745                 750                 755

Pro Gly Glu Asn Pro Gly Ile Thr Ile Asp Glu Trp Leu Leu Lys Asn
                760                 765                 770

Ala Lys Glu Ala Ala Ile Lys Glu Leu Lys Glu Ala Gly Ile Thr Ala
                775                 780                 785

Glu Tyr Leu Phe Asn Leu Ile Asn Lys Ala Lys Thr Val Glu Gly Val
790                 795                 800                 805

Glu Ser Leu Lys Asn Glu Ile Leu Lys Ala His Ala Glu Lys Pro Gly
                810                 815                 820

Glu Asn Pro Gly Ile Thr Ile Asp Glu Trp Leu Leu Lys Asn Ala Lys
                825                 830                 835

Glu Asp Ala Ile Lys Glu Leu Glu Ala Gly Ile Thr Ser Asp Ile
                840                 845                 850

Tyr Phe Asp Ala Ile Asn Lys Ala Lys Thr Ile Glu Gly Val Glu Ala
                855                 860                 865

Leu Lys Asn Glu Ile Leu Lys Ala His Lys Lys Asp Glu Pro Gly
870                 875                 880                 885

Lys Lys Pro Gly Glu Asp Lys Lys Pro Glu Asp Lys Lys Pro Gly Glu
                890                 895                 900
```

```
Asp Lys Lys Pro Glu Asp Lys Lys Pro Gly Glu Asp Lys Lys Pro Glu
            905                 910                 915

Asp Lys Lys Pro Gly Lys Thr Asp Lys Asp Ser Pro Asn Lys Lys Lys
            920                 925                 930

Lys Ala Lys Leu Pro Lys Ala Gly Ser Glu Ala Glu Ile Leu Thr Leu
            935                 940                 945

Ala Ala Ala Ala Leu Ser Thr Ala Ala Gly Ala Tyr Val Ser Leu Lys
950                 955                 960                 965

Lys Pro Lys
```

(2) INFORMATION FOR SEQ ID NO:3:

(i) SEQUENCE CHARACTERISTICS:
        (A) LENGTH: 876 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (v) FRAGMENT TYPE: N-terminal (vi) ORIGINAL SOURCE:
        (A) ORGANISM: Peptostreptococcus
        (B) STRAIN: 1018

(ix) FEATURE:
        (A) NAME/KEY: CDS
        (B) LOCATION: 1..876

(xi) SEQUENCE DESCRIPTION: SEQ ID NO:3:

```
ATG GAA ACA CCA GAA CCA GAA GAA GAA GTT ACA ATC AAA GCT AAC TTA        48
Met Glu Thr Pro Glu Pro Glu Glu Glu Val Thr Ile Lys Ala Asn Leu
 1               5                  10                  15

ATC TTT GCA GAT GGA AGC ACA CAA AAT GCA GAA TTC AAA GGA ACA TTC        96
Ile Phe Ala Asp Gly Ser Thr Gln Asn Ala Glu Phe Lys Gly Thr Phe
            20                  25                  30

GCA AAA GCA GTA TCA GAT GCT TAC GCT TAC GCA GAT GCT TTA AAG AAA       144
Ala Lys Ala Val Ser Asp Ala Tyr Ala Tyr Ala Asp Ala Leu Lys Lys
        35                  40                  45

GAC AAC GGA GAA TAT ACT GTA GAC GTT GCA GAT AAA GGC TTA ACT TTA       192
Asp Asn Gly Glu Tyr Thr Val Asp Val Ala Asp Lys Gly Leu Thr Leu
    50                  55                  60

AAT ATT AAA TTC GCT GGT AAA AAA GAA AAA CCA GAA GAA CCA AAA GAA       240
Asn Ile Lys Phe Ala Gly Lys Lys Glu Lys Pro Glu Glu Pro Lys Glu
65                  70                  75                  80

GAA GTT ACA ATC AAA GTT AAC TTA ATC TTT GCA GAT GGA AAG ACA CAA       288
Glu Val Thr Ile Lys Val Asn Leu Ile Phe Ala Asp Gly Lys Thr Gln
                85                  90                  95

ACA GCA GAA TTC AAA GGA ACA TTT GAA GAA GCA ACA GCA AAA GCT TAT       336
Thr Ala Glu Phe Lys Gly Thr Phe Glu Glu Ala Thr Ala Lys Ala Tyr
            100                 105                 110

GCT TAT GCA GAC TTA TTA GCA AAA GAA AAT GGC GAA TAT ACA GCA GAC       384
Ala Tyr Ala Asp Leu Leu Ala Lys Glu Asn Gly Glu Tyr Thr Ala Asp
        115                 120                 125

TTA GAA GAT GGT GGA AAC ACA ATC AAC ATT AAA TTT GCT GGA AAA GAA       432
Leu Glu Asp Gly Gly Asn Thr Ile Asn Ile Lys Phe Ala Gly Lys Glu
    130                 135                 140

ACA CCA GAA ACA CCA GAA GAA CCA AAA GAA GAA GTT ACA ATC AAA GTT       480
Thr Pro Glu Thr Pro Glu Glu Pro Lys Glu Glu Val Thr Ile Lys Val
```

```
                                                       -continued 145                      150                    155                    160

AAC TTA ATC TTT GCA GAT GGA AAG ATA CAA ACA GCA GAA TTC AAA GGA               528
Asn Leu Ile Phe Ala Asp Gly Lys Ile Gln Thr Ala Glu Phe Lys Gly
                    165                    170                    175

ACA TTT GAA GAA GCA ACA GCA AAA GCT TAT GCT TAT GCA AAC TTA TTA               576
Thr Phe Glu Glu Ala Thr Ala Lys Ala Tyr Ala Tyr Ala Asn Leu Leu
                180                     185                    190

GCA AAA GAA AAT GGC GAA TAT ACA GCA GAC TTA GAA GAT GGT GGA AAC               624
Ala Lys Glu Asn Gly Glu Tyr Thr Ala Asp Leu Glu Asp Gly Gly Asn
                195                     200                    205

ACA ATC AAC ATT AAA TTT GCT GGA AAA GAA ACA CCA GAA ACA CCA GAA               672
Thr Ile Asn Ile Lys Phe Ala Gly Lys Glu Thr Pro Glu Thr Pro Glu
            210                    215                    220

GAA CCA AAA GAA GAA GTT ACA ATC AAA GTT AAC TTA ATC TTT GCA GAT               720
Glu Pro Lys Glu Glu Val Thr Ile Lys Val Asn Leu Ile Phe Ala Asp
225                     230                     235                    240

GGA AAA ACA CAA ACA GCA GAA TTC AAA GGA ACA TTT GAA GAA GCA ACA               768
Gly Lys Thr Gln Thr Ala Glu Phe Lys Gly Thr Phe Glu Glu Ala Thr
                    245                    250                    255

GCA GAA GCT TAC AGA TAT GCA GAC TTA TTA GCA AAA GTA AAT GGT GAA               816
Ala Glu Ala Tyr Arg Tyr Ala Asp Leu Leu Ala Lys Val Asn Gly Glu
                260                    265                    270

TAC ACA GCA GAC TTA GAA GAT GGC GGA TAC ACT ATC AAC ATC AAA TTT               864
Tyr Thr Ala Asp Leu Glu Asp Gly Gly Tyr Thr Ile Asn Ile Lys Phe
                275                    280                    285

GCT GGA AAA TAA                                                               876
Ala Gly Lys
        290

(2) INFORMATION FOR SEQ ID NO:4:

(i) SEQUENCE CHARACTERISTICS:
        (A) LENGTH: 291 amino acids
        (B) TYPE: amino acid
        (D) TOPOLOGY: linear (ii) MOLECULE TYPE: protein (xi) SEQUENCE DESCRIPTION: SEQ ID NO:4:

Met Glu Thr Pro Glu Pro Glu Glu Val Thr Ile Lys Ala Asn Leu
 1               5                  10                  15

Ile Phe Ala Asp Gly Ser Thr Gln Asn Ala Glu Phe Lys Gly Thr Phe
                20                  25                  30

Ala Lys Ala Val Ser Asp Ala Tyr Ala Tyr Ala Asp Ala Leu Lys Lys
            35                  40                  45

Asp Asn Gly Glu Tyr Thr Val Asp Val Ala Asp Lys Gly Leu Thr Leu
        50                  55                  60

Asn Ile Lys Phe Ala Gly Lys Lys Glu Lys Pro Glu Glu Pro Lys Glu
65                  70                  75                  80

Glu Val Thr Ile Lys Val Asn Leu Ile Phe Ala Asp Gly Lys Thr Gln
                85                  90                  95

Thr Ala Glu Phe Lys Gly Thr Phe Glu Glu Ala Thr Ala Lys Ala Tyr
            100                 105                 110

Ala Tyr Ala Asp Leu Leu Ala Lys Glu Asn Gly Glu Tyr Thr Ala Asp
        115                 120                 125

Leu Glu Asp Gly Gly Asn Thr Ile Asn Ile Lys Phe Ala Gly Lys Glu
    130                 135                 140

Thr Pro Glu Thr Pro Glu Glu Pro Lys Glu Glu Val Thr Ile Lys Val
145                 150                 155                 160
```

```
Asn Leu Ile Phe Ala Asp Gly Lys Ile Gln Thr Ala Glu Phe Lys Gly
                165                 170                 175

Thr Phe Glu Glu Ala Thr Ala Lys Ala Tyr Ala Tyr Ala Asn Leu Leu
            180                 185                 190

Ala Lys Glu Asn Gly Glu Tyr Thr Ala Asp Leu Glu Asp Gly Gly Asn
        195                 200                 205

Thr Ile Asn Ile Lys Phe Ala Gly Lys Glu Thr Pro Glu Thr Pro Glu
    210                 215                 220

Glu Pro Lys Glu Val Thr Ile Lys Val Asn Leu Ile Phe Ala Asp
225                 230                 235                 240

Gly Lys Thr Gln Thr Ala Glu Phe Lys Gly Thr Phe Glu Glu Ala Thr
                245                 250                 255

Ala Glu Ala Tyr Arg Tyr Ala Asp Leu Leu Ala Lys Val Asn Gly Glu
                260                 265                 270

Tyr Thr Ala Asp Leu Glu Asp Gly Gly Tyr Thr Ile Asn Ile Lys Phe
            275                 280                 285

Ala Gly Lys
        290

(2) INFORMATION FOR SEQ ID NO:5:

(i) SEQUENCE CHARACTERISTICS:
        (A) LENGTH: 71 amino acids
        (B) TYPE: amino acid
        (C) STRANDEDNESS:
        (D) TOPOLOGY: linear (xi) SEQUENCE DESCRIPTION: SEQ ID NO:5:

Met Glu Thr Pro Glu Pro Glu Glu Glu Val Thr Ile Lys Ala Asn Leu
1               5                   10                  15

Ile Phe Ala Asp Gly Ser Thr Gln Asn Ala Glu Phe Lys Gly Thr Phe
            20                  25                  30

Ala Lys Ala Val Ser Asp Ala Tyr Ala Tyr Ala Asp Ala Leu Lys Lys
        35                  40                  45

Asp Asn Gly Glu Tyr Thr Val Asp Val Ala Asp Lys Gly Leu Thr Leu
    50                  55                  60

Asn Ile Lys Phe Ala Gly Lys
65                  70

(2) INFORMATION FOR SEQ ID NO:6:

(i) SEQUENCE CHARACTERISTICS:
        (A) LENGTH: 71 amino acids
        (B) TYPE: amino acid
        (C) STRANDEDNESS:
        (D) TOPOLOGY: linear (xi) SEQUENCE DESCRIPTION: SEQ ID NO:6:

Lys Glu Lys Pro Glu Glu Pro Lys Glu Glu Val Thr Ile Lys Val Asn
1               5                   10                  15

Leu Ile Phe Ala Asp Gly Lys Thr Gln Thr Ala Glu Phe Lys Gly Thr
            20                  25                  30

Phe Glu Glu Ala Thr Ala Lys Ala Tyr Ala Tyr Ala Asp Leu Leu Ala
        35                  40                  45

Lys Glu Asn Gly Glu Tyr Thr Ala Asp Leu Glu Asp Gly Gly Asn Thr
    50                  55                  60

Ile Asn Ile Lys Phe Ala Gly
65                  70
```

(2) INFORMATION FOR SEQ ID NO:7:

(i) SEQUENCE CHARACTERISTICS:
        (A) LENGTH: 74 amino acids
        (B) TYPE: amino acid
        (C) STRANDEDNESS:
        (D) TOPOLOGY: linear (xi) SEQUENCE DESCRIPTION: SEQ ID NO:7:

Lys Glu Thr Pro Glu Thr Pro Glu Pro Lys Glu Val Thr Ile
1               5                   10                  15

Lys Val Asn Leu Ile Phe Ala Asp Gly Lys Ile Gln Thr Ala Glu Phe
            20                  25                  30

Lys Gly Thr Phe Glu Glu Ala Thr Ala Lys Ala Tyr Ala Tyr Ala Asn
            35                  40                  45

Leu Leu Ala Lys Glu Asn Gly Glu Tyr Thr Ala Asp Leu Glu Asp Gly
        50                  55                  60

Gly Asn Thr Ile Asn Ile Lys Phe Ala Gly
65                  70

(2) INFORMATION FOR SEQ ID NO:8:

(i) SEQUENCE CHARACTERISTICS:
        (A) LENGTH: 75 amino acids
        (B) TYPE: amino acid
        (C) STRANDEDNESS:
        (D) TOPOLOGY: linear (xi) SEQUENCE DESCRIPTION: SEQ ID NO:8:

Lys Glu Thr Pro Glu Thr Pro Glu Pro Lys Glu Val Thr Ile
1               5                   10                  15

Lys Val Asn Leu Ile Phe Ala Asp Gly Lys Thr Gln Thr Ala Glu Phe
            20                  25                  30

Lys Gly Thr Phe Glu Glu Ala Thr Ala Glu Ala Tyr Arg Tyr Ala Asp
            35                  40                  45

Leu Leu Ala Lys Val Asn Gly Glu Tyr Thr Ala Asp Leu Glu Asp Gly
        50                  55                  60

Gly Tyr Thr Ile Asn Ile Lys Phe Ala Gly Lys
65                  70                  75

(2) INFORMATION FOR SEQ ID NO:9:

(i) SEQUENCE CHARACTERISTICS:
        (A) LENGTH: 175 amino acids
        (B) TYPE: amino acid
        (C) STRANDEDNESS:
        (D) TOPOLOGY: linear (xi) SEQUENCE DESCRIPTION: SEQ ID NO:9:

Glu Gln Pro Gly Glu Asn Pro Gly Ile Thr Ile Asp Glu Trp Leu Leu
1               5                   10                  15

Lys Asn Ala Lys Glu Glu Ala Ile Lys Glu Leu Lys Glu Ala Gly Ile
            20                  25                  30

Thr Ser Asp Leu Tyr Phe Ser Leu Ile Asn Lys Ala Lys Thr Val Glu
            35                  40                  45

Gly Val Glu Ala Leu Lys Asn Glu Ile Leu Lys Ala His Ala Gly Glu
        50                  55                  60

Glu Thr Pro Glu Leu Lys Asp Gly Tyr Ala Thr Tyr Glu Glu Ala Glu
65                  70                  75                  80

-continued

```
Ala Ala Ala Lys Glu Ala Leu Lys Asn Asp Asp Val Asn Asn Ala Tyr
            85                  90                  95

Glu Ile Val Gln Gly Ala Asp Gly Arg Tyr Tyr Val Leu Lys Ile
       100                 105                 110

Glu Val Ala Asp Glu Glu Pro Gly Glu Asp Thr Pro Glu Val Gln
           115                 120                 125

Glu Gly Tyr Ala Thr Tyr Glu Glu Ala Glu Ala Ala Lys Glu Ala
       130                 135                 140

Leu Lys Glu Asp Lys Val Asn Asn Ala Tyr Glu Val Val Gln Gly Ala
145                 150                 155                 160

Asp Gly Arg Tyr Tyr Tyr Val Leu Lys Ile Glu Asp Lys Glu Asp
               165                 170                 175
```

(2) INFORMATION FOR SEQ ID NO:10:

(i) SEQUENCE CHARACTERISTICS:
        (A) LENGTH: 66 amino acids
        (B) TYPE: amino acid
        (C) STRANDEDNESS:
        (D) TOPOLOGY: linear (xi) SEQUENCE DESCRIPTION: SEQ ID NO:10:

```
Glu Gln Pro Gly Glu Glu Pro Gly Glu Asn Pro Gly Ile Thr Ile Asp
1               5                   10                  15

Glu Trp Leu Leu Lys Asn Ala Lys Glu Asp Ala Ile Lys Glu Leu Lys
               20                  25                  30

Glu Ala Gly Ile Ser Ser Asp Ile Tyr Phe Asp Ala Ile Asn Lys Ala
           35                  40                  45

Lys Thr Val Glu Gly Val Glu Ala Leu Lys Asn Glu Ile Leu Lys Ala
       50                  55                  60

His Ala
65
```

(2) INFORMATION FOR SEQ ID NO:11:

(i) SEQUENCE CHARACTERISTICS:
        (A) LENGTH: 62 amino acids
        (B) TYPE: amino acid
        (C) STRANDEDNESS:
        (D) TOPOLOGY: linear (xi) SEQUENCE DESCRIPTION: SEQ ID NO:11:

```
Glu Lys Pro Gly Glu Asn Pro Gly Ile Thr Ile Asp Glu Trp Leu Leu
1               5                   10                  15

Lys Asn Ala Lys Glu Ala Ala Ile Lys Glu Leu Lys Glu Ala Gly Ile
               20                  25                  30

Thr Ala Glu Tyr Leu Phe Asn Leu Ile Asn Lys Ala Lys Thr Val Glu
           35                  40                  45

Gly Val Glu Ser Leu Lys Asn Glu Ile Leu Lys Ala His Ala
       50                  55                  60
```

(2) INFORMATION FOR SEQ ID NO:12:

(i) SEQUENCE CHARACTERISTICS:
        (A) LENGTH: 61 amino acids
        (B) TYPE: amino acid
        (C) STRANDEDNESS:
        (D) TOPOLOGY: linear (xi) SEQUENCE DESCRIPTION: SEQ ID NO:12:

```
Glu Lys Pro Gly Glu Asn Pro Gly Ile Thr Ile Asp Glu Trp Leu Leu
```

-continued

```
1               5                    10                   15
Lys Asn Ala Lys Glu Asp Ala Ile Lys Glu Leu Lys Glu Ala Gly Ile
            20                   25                  30

Thr Ser Asp Ile Tyr Phe Asp Ala Ile Asn Lys Ala Lys Thr Ile Glu
        35                   40                  45

Gly Val Glu Ala Leu Lys Asn Glu Ile Leu Lys Ala His
    50                  55                  60
```